US010660641B2

United States Patent
Beardsley

(10) Patent No.: US 10,660,641 B2
(45) Date of Patent: May 26, 2020

(54) ADAPTER WITH CENTERING MECHANISM FOR ARTICULATION JOINT

(71) Applicant: Covidien LP, Mansfield, MA (US)

(72) Inventor: John Beardsley, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 346 days.

(21) Appl. No.: 15/460,361

(22) Filed: Mar. 16, 2017

(65) Prior Publication Data

US 2018/0263608 A1 Sep. 20, 2018

(51) Int. Cl.
*A61B 17/00* (2006.01)
*A61B 17/072* (2006.01)
*A61B 17/29* (2006.01)

(52) U.S. Cl.
CPC ...... *A61B 17/07207* (2013.01); *A61B 2017/0046* (2013.01); *A61B 2017/0069* (2013.01); *A61B 2017/00305* (2013.01); *A61B 2017/00323* (2013.01); *A61B 2017/00473* (2013.01); *A61B 2017/00477* (2013.01); *A61B 2017/07214* (2013.01); *A61B 2017/2903* (2013.01); *A61B 2017/2927* (2013.01); *A61B 2017/2929* (2013.01)

(58) Field of Classification Search
CPC .... A61B 2017/0046; A61B 2017/2927; A61B 2017/2929; A61B 2017/00305; A61B 2017/00473; A61B 2017/0069
USPC .............................. 606/1, 19, 256, 266, 287
See application file for complete search history.

(56) References Cited

U.S. PATENT DOCUMENTS

| 2,777,340 A | 1/1957 | Hettwer et al. |
| 2,957,353 A | 10/1960 | Babacz |
| (Continued) | | |

FOREIGN PATENT DOCUMENTS

| AU | 198654765 | 9/1986 |
| AU | 2008229795 A1 | 4/2009 |
| (Continued) | | |

OTHER PUBLICATIONS

European Search Report dated Dec. 14, 2018, issued in European Appln. No. 18162120.

(Continued)

*Primary Examiner* — Gary Jackson
*Assistant Examiner* — Zahed Kabir
(74) *Attorney, Agent, or Firm* — Carter, DeLuca & Farrell LLP

(57) ABSTRACT

A joint assembly including first and second supports, a spring cage, first and second drive shafts, and first and second cables. The spring cage having a first end fixed to the first support and a second end fixed to the second support and defining a spring channel between the first and second supports. The first drive shaft rotatably disposed along a first longitudinal axis defined by the first support and the second drive shaft rotatably disposed along a second longitudinal axis defined by the second support. The first and second cables extending through the first support and having an end secured to the second support. The first and second cables translatable in a direction parallel to the first longitudinal axis to articulated the second support relative to the first support such that the second longitudinal axis is disposed at a total joint angle relative to the first longitudinal axis.

15 Claims, 16 Drawing Sheets

(56) References Cited

U.S. PATENT DOCUMENTS

| | | |
|---|---|---|
| 3,079,606 A | 3/1963 | Bobrov et al. |
| 3,111,328 A | 11/1963 | Di Rito et al. |
| 3,490,675 A | 1/1970 | Green et al. |
| 3,499,591 A | 3/1970 | Green |
| 3,695,058 A | 10/1972 | Keith, Jr. |
| 3,734,515 A | 5/1973 | Dudek |
| 3,759,336 A | 9/1973 | Marcovitz et al. |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,162,399 A | 7/1979 | Hudson |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,606,343 A | 8/1986 | Conta et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,705,038 A | 11/1987 | Sjostrom et al. |
| 4,722,685 A | 2/1988 | de Estrada et al. |
| 4,728,020 A | 3/1988 | Green et al. |
| 4,752,024 A | 6/1988 | Green et al. |
| 4,784,137 A | 11/1988 | Kulik et al. |
| 4,823,807 A | 4/1989 | Russell et al. |
| 4,863,088 A | 9/1989 | Redmond et al. |
| 4,869,415 A | 9/1989 | Fox |
| 4,874,181 A | 10/1989 | Hsu |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,118 A | 7/1992 | Walmesley |
| 5,129,570 A | 7/1992 | Schulze et al. |
| 5,141,144 A | 8/1992 | Foslien et al. |
| 5,152,744 A | 10/1992 | Krause et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,301,061 A | 4/1994 | Nakada et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,350,355 A | 9/1994 | Sklar |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,400,267 A | 3/1995 | Denen et al. |
| 5,403,312 A | 4/1995 | Yates et al. |
| 5,405,072 A | 4/1995 | Zlock et al. |
| 5,407,293 A | 4/1995 | Crainich |
| 5,411,508 A | 5/1995 | Bessler et al. |
| 5,413,267 A | 5/1995 | Solyntjes et al. |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,427,087 A | 6/1995 | Ito et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,476,379 A | 12/1995 | Disel |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |

(56) References Cited

U.S. PATENT DOCUMENTS

| | | |
|---|---|---|
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,609,560 A | 3/1997 | Ichikawa et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,693,042 A | 12/1997 | Boiarski et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,762,603 A | 6/1998 | Thompson |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,792,573 A | 8/1998 | Pitzen et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,863,159 A | 1/1999 | Lasko |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,908,427 A | 6/1999 | McKean et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 5,993,454 A | 11/1999 | Longo |
| 6,004,335 A | 12/1999 | Vaitekunas et al. |
| 6,010,054 A | 1/2000 | Johnson et al. |
| 6,013,991 A | 1/2000 | Philipp |
| 6,017,354 A | 1/2000 | Culp et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,090,123 A | 7/2000 | Culp et al. |
| 6,099,551 A | 8/2000 | Gabbay |

(56) References Cited

U.S. PATENT DOCUMENTS

| | | |
|---|---|---|
| 6,109,500 A | 8/2000 | Alli et al. |
| 6,126,651 A | 10/2000 | Mayer |
| 6,129,547 A | 10/2000 | Cise et al. |
| 6,131,789 A | 10/2000 | Schulze et al. |
| 6,131,790 A | 10/2000 | Piraka |
| 6,155,473 A | 12/2000 | Tompkins et al. |
| 6,165,169 A | 12/2000 | Panescu et al. |
| 6,197,017 B1 | 3/2001 | Brock et al. |
| 6,202,914 B1 | 3/2001 | Geiste et al. |
| 6,239,732 B1 | 5/2001 | Cusey |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,302,311 B1 | 10/2001 | Adams et al. |
| 6,315,183 B1 | 11/2001 | Piraka |
| 6,315,184 B1 | 11/2001 | Whitman |
| 6,321,855 B1 | 11/2001 | Barnes |
| 6,325,810 B1 | 12/2001 | Hamilton et al. |
| 6,329,778 B1 | 12/2001 | Culp et al. |
| 6,330,965 B1 | 12/2001 | Milliman et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,391,038 B2 | 5/2002 | Vargas et al. |
| 6,398,797 B2 | 6/2002 | Bombard et al. |
| 6,434,507 B1 | 8/2002 | Clayton et al. |
| 6,436,097 B1 | 8/2002 | Nardella |
| 6,439,446 B1 | 8/2002 | Perry et al. |
| 6,443,973 B1 | 9/2002 | Whitman |
| 6,461,372 B1 | 10/2002 | Jensen et al. |
| 6,478,804 B2 | 11/2002 | Vargas et al. |
| 6,488,196 B1 | 12/2002 | Fenton, Jr. |
| 6,488,197 B1 | 12/2002 | Whitman |
| 6,491,201 B1 | 12/2002 | Whitman |
| 6,503,257 B2 | 1/2003 | Grant et al. |
| 6,505,768 B2 | 1/2003 | Whitman |
| 6,533,157 B1 | 3/2003 | Whitman |
| 6,537,280 B2 | 3/2003 | Dinger et al. |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,610,066 B2 | 8/2003 | Dinger et al. |
| 6,611,793 B1 | 8/2003 | Burnside et al. |
| 6,619,529 B2 | 9/2003 | Green et al. |
| D480,808 S | 10/2003 | Wells et al. |
| 6,644,532 B2 | 11/2003 | Green et al. |
| 6,645,218 B1 | 11/2003 | Cassidy et al. |
| 6,654,999 B2 | 12/2003 | Stoddard et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,699,177 B1 | 3/2004 | Wang et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,743,240 B2 | 6/2004 | Smith et al. |
| 6,755,338 B2 | 6/2004 | Hahnen et al. |
| 6,783,524 B2 | 8/2004 | Anderson et al. |
| 6,783,533 B2 | 8/2004 | Green et al. |
| 6,786,382 B1 | 9/2004 | Hoffman |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,860,892 B1 | 3/2005 | Tanaka et al. |
| 6,877,647 B2 | 4/2005 | Green et al. |
| 6,889,116 B2 | 5/2005 | Jinno |
| 6,899,538 B2 | 5/2005 | Matoba |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| RE39,152 E | 6/2006 | Aust et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,021 B1 | 7/2007 | Johnson |
| 7,238,195 B2 | 7/2007 | Viola |
| 7,246,734 B2 | 7/2007 | Shelton, IV |
| 7,252,660 B2 | 8/2007 | Kunz |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |

(56) References Cited

U.S. PATENT DOCUMENTS

| | | |
|---|---|---|
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,549,564 B2 | 6/2009 | Boudreaux |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,699,835 B2 | 4/2010 | Lee et al. |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,758,613 B2 | 7/2010 | Whitman |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |

(56) References Cited

U.S. PATENT DOCUMENTS

| | | |
|---|---|---|
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,822,458 B2 | 10/2010 | Webster, III et al. |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,905,897 B2 | 3/2011 | Whitman et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,922,719 B2 | 4/2011 | Ralph et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,947,034 B2 | 5/2011 | Whitman |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,951,071 B2 | 5/2011 | Whitman et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,020,742 B2 | 9/2011 | Marczyk |
| 8,020,743 B2 | 9/2011 | Shelton, IV |
| 8,025,199 B2 | 9/2011 | Whitman et al. |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,035,487 B2 | 10/2011 | Malackowski |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |

(56) References Cited

U.S. PATENT DOCUMENTS

| | | |
|---|---|---|
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,114,118 B2 | 2/2012 | Knodel et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,152,516 B2 | 4/2012 | Harvey et al. |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,182,494 B1 | 5/2012 | Yencho et al. |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,186,587 B2 | 5/2012 | Zmood et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,367 B2 | 7/2012 | Hsu |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,292,888 B2 | 10/2012 | Whitman |
| 8,303,581 B2 | 11/2012 | Arts et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,855 B2 | 1/2013 | Hillely et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,144 B2 | 1/2013 | Whitman et al. |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,633 B2 | 2/2013 | Simaan et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,057 B2 | 2/2013 | Cude et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |

(56) References Cited

U.S. PATENT DOCUMENTS

| | | |
|---|---|---|
| 8,388,652 B2 | 3/2013 | Viola |
| 8,391,957 B2 | 3/2013 | Carlson et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,926 B2 | 3/2013 | Nobis et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,585 B2 | 6/2013 | Whitman |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,551,076 B2 | 10/2013 | Duval et al. |
| 8,556,151 B2 | 10/2013 | Viola |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,287 B2 | 12/2013 | Yates et al. |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | Stopek et al. |
| 8,623,000 B2 | 1/2014 | Humayun et al. |
| 8,627,994 B2 | 1/2014 | Zemlok et al. |
| 8,627,995 B2 | 1/2014 | Smith et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,463 B2 | 1/2014 | Drinan et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,696,552 B2 | 4/2014 | Whitman |
| 8,701,958 B2 | 4/2014 | Shelton, IV et al. |
| 8,701,959 B2 | 4/2014 | Shah |
| 8,701,961 B2 | 4/2014 | Ivanko |

(56) References Cited

U.S. PATENT DOCUMENTS

| | | |
|---|---|---|
| 8,708,213 B2 | 4/2014 | Shelton, IV et al. |
| 8,714,429 B2 | 5/2014 | Demmy |
| 8,715,277 B2 | 5/2014 | Weizman |
| 8,715,306 B2 | 5/2014 | Faller et al. |
| 8,720,766 B2 | 5/2014 | Hess |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,858,571 B2 | 10/2014 | Shelton, IV et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,905,289 B2 | 12/2014 | Patel et al. |
| 8,919,630 B2 | 12/2014 | Milliman |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,680 B2 | 1/2015 | Milliman |
| 8,931,682 B2 | 1/2015 | Timm et al. |
| 8,931,693 B1 | 1/2015 | Kumar et al. |
| 8,939,344 B2 | 1/2015 | Olson et al. |
| 8,950,646 B2 | 2/2015 | Viola |
| 8,955,732 B2 | 2/2015 | Zemlok et al. |
| 8,958,429 B2 | 2/2015 | Shukla et al. |
| 8,960,517 B2 | 2/2015 | Lee |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,992,422 B2 | 3/2015 | Spivey et al. |
| 8,998,060 B2 | 4/2015 | Bruewer et al. |
| 9,005,230 B2 | 4/2015 | Yates et al. |
| 9,010,607 B2 | 4/2015 | Kostrzewski |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,016,546 B2 | 4/2015 | Demmy et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,033,203 B2 | 5/2015 | Woodard, Jr. et al. |
| 9,033,868 B2 | 5/2015 | Whitman et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,055,943 B2 | 6/2015 | Zemlok et al. |
| 9,060,770 B2 | 6/2015 | Shelton, IV et al. |
| 9,064,653 B2 | 6/2015 | Prest et al. |
| 9,072,515 B2 | 7/2015 | Hall et al. |
| 9,072,535 B2 | 7/2015 | Shelton, IV et al. |
| 9,089,326 B2 | 7/2015 | Krumanaker et al. |
| 9,101,359 B2 | 8/2015 | Smith et al. |
| 9,107,663 B2 | 8/2015 | Swensgard |
| 9,107,664 B2 | 8/2015 | Marczyk |
| 9,113,847 B2 | 8/2015 | Whitman et al. |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,875 B2 | 8/2015 | Viola et al. |
| 9,113,876 B2 | 8/2015 | Zemlok et al. |
| 9,113,880 B2 | 8/2015 | Zemlok et al. |
| 9,113,899 B2 | 8/2015 | Garrison et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,661 B2 | 12/2015 | Swensgard |
| 9,204,876 B2 | 12/2015 | Cappola et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,277,919 B2 | 3/2016 | Timmer et al. |
| 9,282,961 B2 | 3/2016 | Whitman et al. |
| 9,282,962 B2 | 3/2016 | Schmid et al. |
| 9,282,963 B2 | 3/2016 | Bryant |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,295,522 B2 | 3/2016 | Kostrzewski |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |

(56) References Cited

U.S. PATENT DOCUMENTS

| | | |
|---|---|---|
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,539,007 B2 | 1/2017 | Dhakad et al. |
| 9,549,735 B2 | 1/2017 | Shelton, IV et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0108357 A1 | 6/2004 | Milliman et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0125027 A1 | 6/2005 | Knodel et al. |
| 2005/0131442 A1 | 6/2005 | Yachia et al. |
| 2005/0216055 A1 | 9/2005 | Scirica et al. |
| 2006/0049229 A1 | 3/2006 | Milliman et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0180634 A1 | 8/2006 | Shelton et al. |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0152014 A1 | 7/2007 | Gillum et al. |
| 2007/0170225 A1 | 7/2007 | Shelton et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0078802 A1 | 4/2008 | Hess et al. |
| 2008/0109012 A1 | 5/2008 | Falco et al. |
| 2008/0110958 A1 | 5/2008 | McKenna et al. |
| 2008/0110961 A1 | 5/2008 | Voegele et al. |
| 2008/0147089 A1 | 6/2008 | Loh et al. |
| 2008/0167736 A1 | 7/2008 | Swayze et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0012533 A1 | 1/2009 | Barbagli et al. |
| 2009/0090763 A1 | 4/2009 | Zemlok et al. |
| 2009/0090766 A1 | 4/2009 | Knodel |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0242610 A1 | 10/2009 | Shelton, IV et al. |
| 2009/0254094 A1 | 10/2009 | Knapp et al. |
| 2009/0255974 A1 | 10/2009 | Viola |
| 2009/0299141 A1 | 12/2009 | Downey et al. |
| 2009/0308907 A1 | 12/2009 | Nalagatla et al. |
| 2010/0012703 A1 | 1/2010 | Calabrese et al. |
| 2010/0023022 A1 | 1/2010 | Zeiner et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0193568 A1 | 8/2010 | Scheib et al. |
| 2010/0211053 A1 | 8/2010 | Ross et al. |
| 2010/0224668 A1 | 9/2010 | Fontayne et al. |
| 2010/0225073 A1 | 9/2010 | Porter et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0017801 A1 | 1/2011 | Zemlok et al. |
| 2011/0024477 A1 | 2/2011 | Hall |
| 2011/0024478 A1 | 2/2011 | Shelton, IV |

(56) References Cited

U.S. PATENT DOCUMENTS

| | | |
|---|---|---|
| 2011/0036891 A1 | 2/2011 | Zemlok et al. |
| 2011/0071508 A1 | 3/2011 | Duval et al. |
| 2011/0077673 A1 | 3/2011 | Grubac et al. |
| 2011/0087276 A1 | 4/2011 | Bedi et al. |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0147433 A1 | 6/2011 | Shelton, IV et al. |
| 2011/0155783 A1 | 6/2011 | Rajappa et al. |
| 2011/0155786 A1 | 6/2011 | Shelton, IV |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0172648 A1 | 7/2011 | Jeong |
| 2011/0174099 A1 | 7/2011 | Ross et al. |
| 2011/0184245 A1 | 7/2011 | Xia et al. |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0278343 A1 | 11/2011 | Knodel et al. |
| 2011/0290854 A1 | 12/2011 | Timm et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0016362 A1 | 1/2012 | Heinrich et al. |
| 2012/0022554 A1* | 1/2012 | Paik .................... A61B 17/29 606/130 |
| 2012/0053406 A1 | 3/2012 | Conlon et al. |
| 2012/0061446 A1 | 3/2012 | Knodel et al. |
| 2012/0074199 A1 | 3/2012 | Olson et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0089131 A1 | 4/2012 | Zemlok et al. |
| 2012/0091183 A1 | 4/2012 | Manoux et al. |
| 2012/0104071 A1 | 5/2012 | Bryant |
| 2012/0116368 A1 | 5/2012 | Viola |
| 2012/0138659 A1 | 6/2012 | Marczyk et al. |
| 2012/0143002 A1 | 6/2012 | Aranyi et al. |
| 2012/0172924 A1 | 7/2012 | Allen, IV |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0209253 A1 | 8/2012 | Donhowe |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0245428 A1 | 9/2012 | Smith et al. |
| 2012/0248169 A1 | 10/2012 | Widenhouse et al. |
| 2012/0253326 A1 | 10/2012 | Kleyman |
| 2012/0253329 A1 | 10/2012 | Zemlok et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023923 A1* | 1/2013 | Mueller .................... A61B 17/29 606/205 |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0092717 A1 | 4/2013 | Marczyk et al. |
| 2013/0093149 A1 | 4/2013 | Saur et al. |
| 2013/0098964 A1 | 4/2013 | Smith et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0178838 A1* | 7/2013 | Malkowski .............. A61B 17/00 606/1 |
| 2013/0181035 A1 | 7/2013 | Milliman |
| 2013/0184704 A1 | 7/2013 | Beardsley et al. |
| 2013/0193188 A1 | 8/2013 | Shelton, IV et al. |
| 2013/0214025 A1 | 8/2013 | Zemlok et al. |
| 2013/0240596 A1 | 9/2013 | Whitman |
| 2013/0256380 A1 | 10/2013 | Schmid et al. |
| 2013/0274722 A1 | 10/2013 | Kostrzewski et al. |
| 2013/0277410 A1 | 10/2013 | Fernandez et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334280 A1 | 12/2013 | Krehel et al. |
| 2013/0334281 A1 | 12/2013 | Williams |
| 2013/0344970 A1 | 12/2013 | Kramer et al. |
| 2014/0005662 A1 | 1/2014 | Shelton, IV |
| 2014/0012236 A1 | 1/2014 | Williams et al. |
| 2014/0012237 A1 | 1/2014 | Pribanic et al. |
| 2014/0012238 A1 | 1/2014 | Chen et al. |
| 2014/0012289 A1 | 1/2014 | Snow et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0025046 A1 | 1/2014 | Williams et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0110455 A1 | 4/2014 | Ingmanson et al. |
| 2014/0114403 A1 | 4/2014 | Dale et al. |
| 2014/0131419 A1 | 5/2014 | Bettuchi |
| 2014/0138423 A1 | 5/2014 | Whitfield et al. |
| 2014/0144970 A1 | 5/2014 | Aranyi et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |

(56) References Cited

U.S. PATENT DOCUMENTS

| | | |
|---|---|---|
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0276932 A1 | 9/2014 | Williams et al. |
| 2014/0284371 A1 | 9/2014 | Morgan et al. |
| 2014/0291379 A1 | 10/2014 | Schellin et al. |
| 2014/0291380 A1 | 10/2014 | Weaner et al. |
| 2014/0291383 A1 | 10/2014 | Spivey et al. |
| 2014/0299647 A1 | 10/2014 | Scirica et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0367445 A1 | 12/2014 | Ingmanson et al. |
| 2014/0367446 A1 | 12/2014 | Ingmanson et al. |
| 2014/0373652 A1 | 12/2014 | Zergiebel et al. |
| 2015/0014392 A1 | 1/2015 | Williams et al. |
| 2015/0048143 A1 | 2/2015 | Scheib et al. |
| 2015/0048144 A1 | 2/2015 | Whitman |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0133957 A1 | 5/2015 | Kostrzewski |
| 2015/0133996 A1 | 5/2015 | Shelton, IV et al. |
| 2015/0134076 A1 | 5/2015 | Shelton, IV et al. |
| 2015/0150547 A1 | 6/2015 | Ingmanson et al. |
| 2015/0150556 A1 | 6/2015 | McCuen |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0182220 A1 | 7/2015 | Yates et al. |
| 2015/0201931 A1 | 7/2015 | Zergiebel et al. |
| 2015/0209040 A1 | 7/2015 | Whitman et al. |
| 2015/0250474 A1 | 9/2015 | Abbott et al. |
| 2015/0272577 A1 | 10/2015 | Zemlok et al. |
| 2015/0297199 A1 | 10/2015 | Nicholas et al. |
| 2015/0297225 A1 | 10/2015 | Huitema et al. |
| 2015/0303996 A1 | 10/2015 | Calderoni |
| 2015/0316431 A1 | 11/2015 | Collins et al. |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2015/0374449 A1 | 12/2015 | Chowaniec et al. |
| 2015/0380187 A1 | 12/2015 | Zergiebel et al. |
| 2016/0030040 A1 | 2/2016 | Calderoni et al. |
| 2016/0051259 A1 | 2/2016 | Hopkins et al. |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0095596 A1 | 4/2016 | Scirica et al. |
| 2016/0100835 A1 | 4/2016 | Linder et al. |
| 2016/0106406 A1 | 4/2016 | Cabrera et al. |
| 2016/0113647 A1 | 4/2016 | Hodgkinson |
| 2016/0113648 A1 | 4/2016 | Zergiebel et al. |
| 2016/0113649 A1 | 4/2016 | Zergiebel et al. |
| 2016/0120542 A1 | 5/2016 | Westling et al. |
| 2016/0166249 A1 | 6/2016 | Knodel |
| 2016/0166253 A1 | 6/2016 | Knodel |
| 2016/0199064 A1 | 7/2016 | Shelton, IV et al. |
| 2016/0199084 A1 | 7/2016 | Takei |
| 2016/0206315 A1 | 7/2016 | Olson |
| 2016/0206336 A1 | 7/2016 | Frushour |
| 2016/0235494 A1 | 8/2016 | Shelton, IV et al. |
| 2016/0242773 A1 | 8/2016 | Sadowski et al. |
| 2016/0242774 A1 | 8/2016 | Ebner |
| 2016/0242779 A1 | 8/2016 | Aranyi et al. |
| 2016/0249915 A1 | 9/2016 | Beckman et al. |
| 2016/0249916 A1 | 9/2016 | Shelton, IV et al. |
| 2016/0249918 A1 | 9/2016 | Shelton, IV et al. |
| 2016/0249927 A1 | 9/2016 | Beckman et al. |
| 2016/0249929 A1 | 9/2016 | Cappola et al. |
| 2016/0249945 A1 | 9/2016 | Shelton, IV et al. |
| 2016/0256071 A1 | 9/2016 | Shelton, IV et al. |
| 2016/0256152 A1 | 9/2016 | Kostrzewski |
| 2016/0256154 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256187 A1 | 9/2016 | Shelton, IV et al. |
| 2016/0262750 A1 | 9/2016 | Hausen et al. |
| 2016/0270783 A1 | 9/2016 | Yigit et al. |
| 2016/0270788 A1 | 9/2016 | Czernik |

(56) References Cited

U.S. PATENT DOCUMENTS

| | | |
|---|---|---|
| 2016/0278764 A1 | 9/2016 | Shelton, IV et al. |
| 2016/0278765 A1 | 9/2016 | Shelton, IV et al. |
| 2016/0278771 A1 | 9/2016 | Shelton, IV et al. |
| 2016/0278774 A1 | 9/2016 | Shelton, IV et al. |
| 2016/0278775 A1 | 9/2016 | Shelton, IV et al. |
| 2016/0278777 A1 | 9/2016 | Shelton, IV et al. |
| 2016/0278848 A1 | 9/2016 | Boudreaux et al. |
| 2016/0287250 A1 | 10/2016 | Shelton, IV et al. |
| 2016/0287251 A1 | 10/2016 | Shelton, IV et al. |
| 2016/0296216 A1* | 10/2016 | Nicholas ............... A61B 17/00 |
| 2016/0296226 A1 | 10/2016 | Kostrzewski |
| 2016/0302791 A1 | 10/2016 | Schmitt |
| 2016/0310134 A1 | 10/2016 | Contini et al. |
| 2016/0324514 A1 | 11/2016 | Srinivas et al. |
| 2016/0324518 A1 | 11/2016 | Nicholas et al. |
| 2016/0338703 A1 | 11/2016 | Scirica et al. |
| 2016/0345971 A1 | 12/2016 | Bucciaglia et al. |
| 2016/0345973 A1 | 12/2016 | Marczyk et al. |
| 2016/0354176 A1 | 12/2016 | Schmitt |
| 2016/0374678 A1 | 12/2016 | Becerra et al. |
| 2017/0000483 A1 | 1/2017 | Motai et al. |
| 2017/0020525 A1 | 1/2017 | Shah |
| 2017/0105746 A1* | 4/2017 | O'Keefe ............ A61B 17/2909 |

FOREIGN PATENT DOCUMENTS

| | | |
|---|---|---|
| CA | 2451558 A1 | 1/2003 |
| CA | 2773414 A1 | 11/2012 |
| CA | 2824590 A1 | 4/2014 |
| CA | 2884962 A1 | 11/2015 |
| CN | 101856251 A | 10/2010 |
| CN | 102247182 A | 11/2011 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| DE | 102008053842 A1 | 5/2010 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0634144 A1 | 1/1995 |
| EP | 0648476 A1 | 4/1995 |
| EP | 0656188 A2 | 6/1995 |
| EP | 0666057 A2 | 8/1995 |
| EP | 0686374 A2 | 12/1995 |
| EP | 0705571 A1 | 4/1996 |
| EP | 0 760 230 A1 | 3/1997 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1 813 203 A2 | 8/2007 |
| EP | 1813199 A1 | 8/2007 |
| EP | 1813212 A1 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2090253 A2 | 8/2009 |
| EP | 2090254 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 A2 | 6/2012 |
| EP | 2491872 A1 | 8/2012 |
| EP | 2583630 A2 | 4/2013 |
| EP | 2586382 A2 | 5/2013 |
| EP | 2606834 A2 | 6/2013 |
| EP | 2649948 A1 | 10/2013 |
| EP | 2668910 A2 | 12/2013 |
| EP | 2676615 A2 | 12/2013 |
| EP | 2815705 A1 | 12/2014 |
| EP | 2907456 A1 | 8/2015 |
| EP | 2937047 A1 | 10/2015 |
| EP | 3192455 A1 | 7/2017 |
| EP | 3369384 A2 * | 9/2018 | .......... F16C 11/0695 |
| ES | 2333509 A1 | 2/2010 |
| FR | 391239 A | 10/1908 |
| FR | 2542188 A1 | 9/1984 |
| FR | 2660851 A1 | 10/1991 |
| FR | 2681775 A1 | 4/1993 |
| FR | 2861574 A1 | 5/2005 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51-149985 | 12/1976 |
| JP | 08-038488 | 2/1996 |
| JP | 2001-87272 | 4/2001 |
| JP | 2005-125075 A | 5/2005 |
| KR | 20120022521 A | 3/2012 |
| SU | 659146 A1 | 4/1979 |
| SU | 728848 A1 | 4/1980 |
| SU | 980703 A1 | 12/1982 |

(56) References Cited

FOREIGN PATENT DOCUMENTS

| | | |
|---|---|---|
| SU | 990220 A1 | 1/1983 |
| WO | 08302247 | 7/1983 |
| WO | 89/10094 A1 | 11/1989 |
| WO | 9210976 A1 | 7/1992 |
| WO | 9308754 A1 | 5/1993 |
| WO | 9314706 A1 | 8/1993 |
| WO | 99/15086 A1 | 4/1999 |
| WO | 2000/072760 A1 | 12/2000 |
| WO | 2000/072765 A1 | 12/2000 |
| WO | 2003/000138 A2 | 1/2003 |
| WO | 03001986 A2 | 1/2003 |
| WO | 2003/026511 A1 | 4/2003 |
| WO | 2003/030743 A2 | 4/2003 |
| WO | 2003065916 A1 | 8/2003 |
| WO | 2003/077769 A1 | 9/2003 |
| WO | 2003090630 A2 | 11/2003 |
| WO | 2004/032760 A2 | 4/2004 |
| WO | 2004/107989 A1 | 12/2004 |
| WO | 2006/042210 A2 | 4/2006 |
| WO | 2007016290 A2 | 2/2007 |
| WO | 2007/026354 A1 | 3/2007 |
| WO | 2007137304 A2 | 11/2007 |
| WO | 2008/008178 A2 | 1/2008 |
| WO | 2008/020964 A2 | 2/2008 |
| WO | 2008/131362 A2 | 10/2008 |
| WO | 2008/133956 A2 | 11/2008 |
| WO | 2009/039506 A1 | 3/2009 |
| WO | 2007014355 A3 | 4/2009 |
| WO | 2009071070 A2 | 6/2009 |
| WO | 2009/132359 A2 | 10/2009 |
| WO | 2009/143092 A1 | 11/2009 |
| WO | 2009149234 A1 | 12/2009 |
| WO | 2010/112609 A1 | 10/2010 |
| WO | 2011/108840 A2 | 9/2011 |
| WO | 2012/040984 A1 | 4/2012 |
| WO | 20150191887 A1 | 12/2015 |
| WO | 2016161449 A1 | 10/2016 |

OTHER PUBLICATIONS

European Office Action dated Oct. 24, 2019, issued in EP Appln. No. 18 162 120.

\* cited by examiner

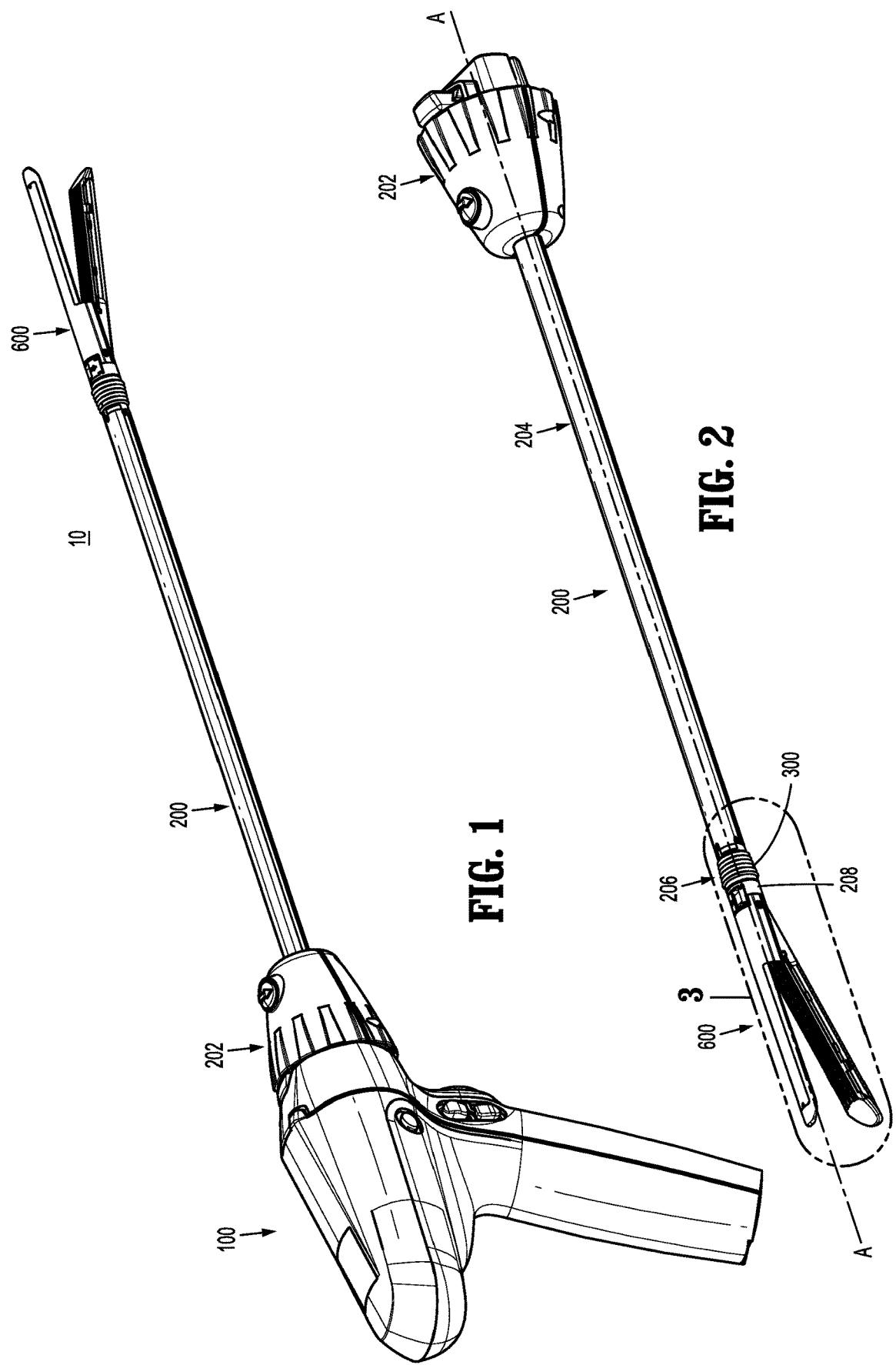

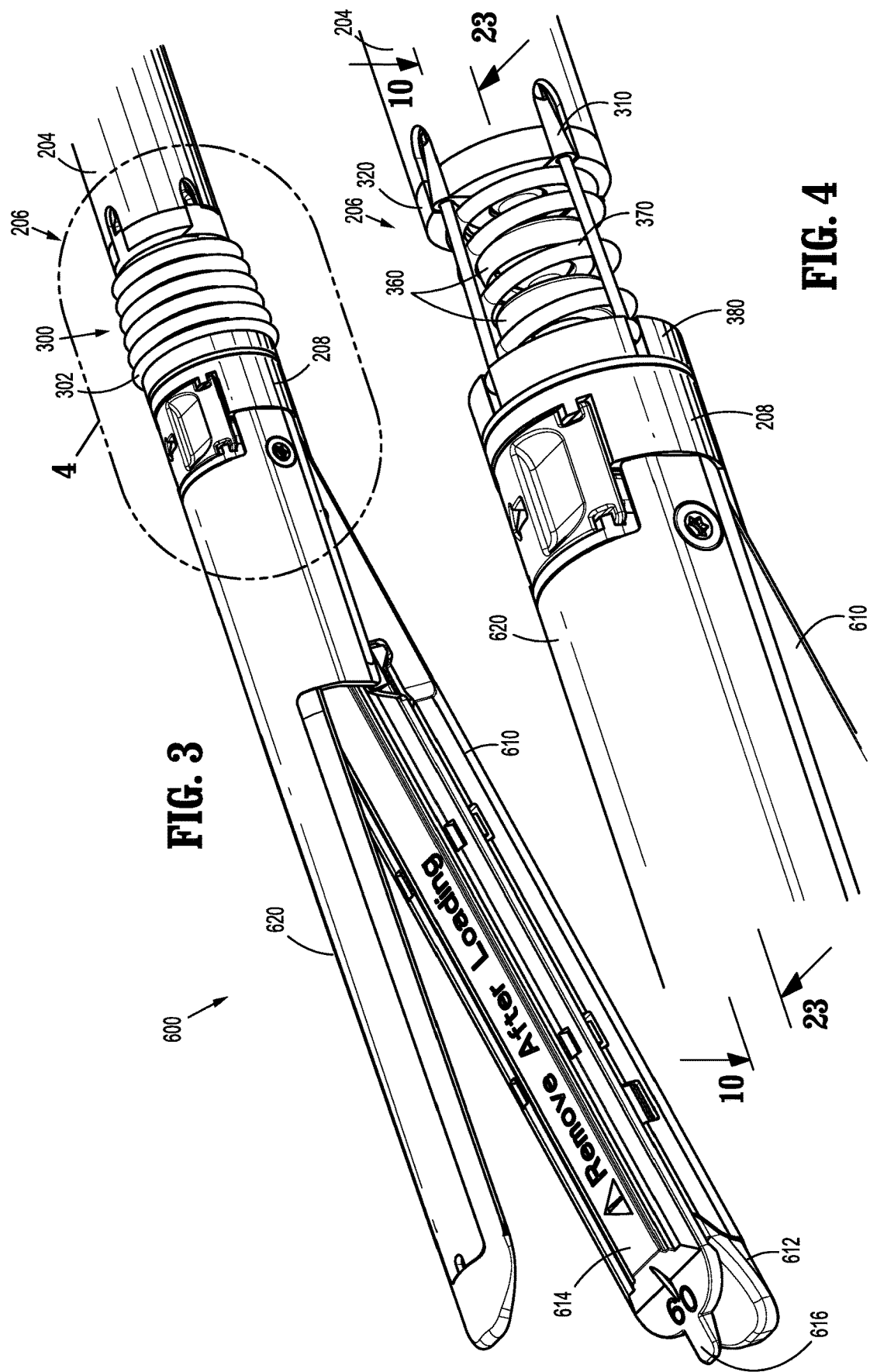

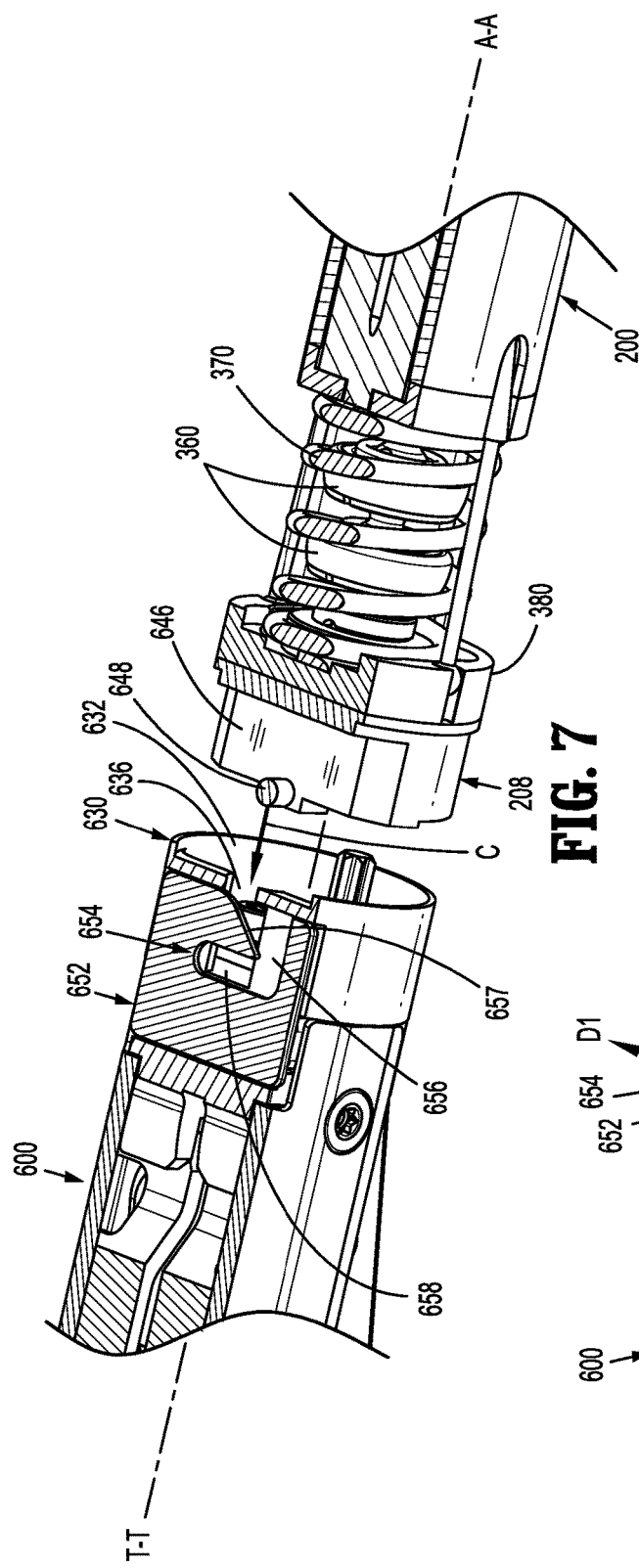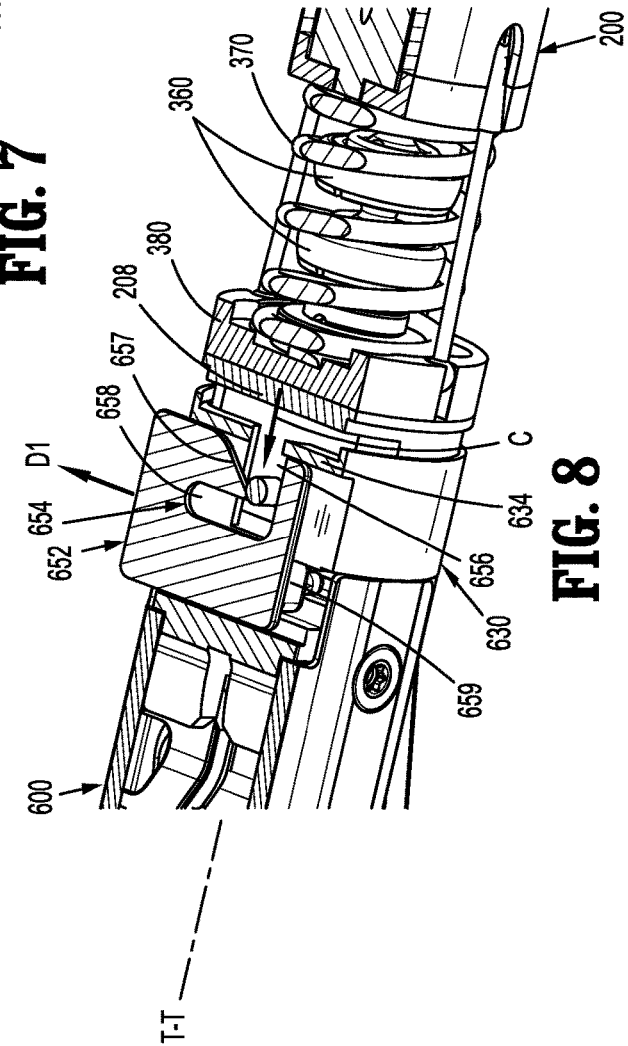

ADAPTER WITH CENTERING MECHANISM FOR ARTICULATION JOINT

BACKGROUND

1. Technical Field

The present disclosure relates to surgical instruments and, more specifically, to centering mechanisms for articulation joints of surgical instruments.

2. Discussion of Related Art

A number of surgical instrument manufacturers have developed product lines with proprietary powered drive systems for operating and/or manipulating surgical instruments. In many instances, the surgical instruments include a powered handle assembly, which is reusable, and a disposable end effector or the like that is releasably connected to the powered handle assembly prior to use and then disconnected from the end effector following use in order to be disposed of or in some instances resterilized for re-use.

Generally, adapters of existing surgical instruments translate and deliver power from the handle assemblies, electromechanically or manually, to the end effectors. The adapters may support an articulation joint or joints for articulating the end effectors relative to a longitudinal axis of the adapter. To improve accessibility to a surgical site, the articulation joints may be configured to articulate the end effector about a variety of axes in relation to the longitudinal axis of the adapter and may include multiple joints or a universal joint to achieve a desired articulation angle for the end effector.

When an articulation joint of an articulation mechanism includes a plurality of axes of articulation, the degree of articulation can be difficult to accurately control because when a force is applied to articulate the end effector, the end effector is articulated about the plurality of axes simultaneously. In addition, during actuation of the surgical instrument, the position of the articulation joints relative to one another can vary in response to forces exerted between the handle and the end effector which pass through the joints. There is a continuing need to improve the accuracy of the articulation mechanisms of adapters supporting end effectors for articulation about a plurality of axes.

SUMMARY

In an aspect of the present disclosure, a joint assembly includes a first support, a second support, a first drive shaft, a second drive shaft, a first link and a spring cage. The first support defines a first longitudinal axis and the second support defines a second longitudinal axis. The first drive shaft is rotatably disposed along the first longitudinal axis and extends through the first support. The second drive shaft is rotatably disposed along the second longitudinal axis and extends through the second support. The first link is disposed between and is coupled to each of the first and second drive shafts such that the first link rotates in response to rotation of the first drive shaft and the second drive shaft rotates in response to rotation of the first link. The spring cage has a first end that is fixed to the first support and a second end that is fixed to the second support. The spring cage defines a spring channel between the first and second supports such that the first link and a portion of the first and second drive shafts are disposed within the spring channel. The spring cage engages the first link to effect uniform articulation across the joint assembly in response to articulation of the second support relative to the first support.

In aspects, the spring cage urges the first and second supports towards an aligned position in which the first and second longitudinal axes are coaxially aligned.

In some aspects, the joint assembly includes a second link disposed between and coupled to the first link and the second drive shaft. Rotation of the first link may cause rotation of the second link to cause rotation of the second drive shaft. The spring cage may engage the second link to effect uniform articulation across the joint assembly in response to articulation of the second support relative to the first support.

In some aspects, the first link defines a cavity that pivotally receives a portion of the first drive shaft and includes a distal ball. The first link may define a first link axis that is coaxial with the first and second longitudinal axes in the aligned position. The spring cage may control the first link in response to articulation of the second support relative to the first support such that the first link axis defines a first joint angle relative to the first longitudinal axis.

In certain aspects, the joint assembly includes a link guide that is disposed about the first link. The link guide may be directly engaged by the spring cage during articulation of the second support in relation to the first support to position the first link. The link guide may include an inner collar and an outer collar. The inner collar may form a split ring that defines a gap. The outer collar may include an inner surface and may be received over the ring of the inner collar such that the inner surface of the outer collar engages the ring of the inner collar to reduce the gap to secure the ling guide to the first link. The first link may define a disc that is positioned between the cavity and the distal ball. The disc may be disposed orthogonal to the first link axis and the ring of the inner collar may define a groove that receives the disc to longitudinally secure the link guide relative to the first link. The inner collar may be formed of a resilient material and may be biased outwardly such that engagement between the ring of the inner collar and the inner surface of the outer collar fixes the inner and outer collars relative to one another. Wherein the inner collar is formed to a plastic and the outer collar is formed of a metal. The inner and outer collars may be formed of a plastic. The outer collar may include an outer surface having a friction reducing coating. The second disk may define a cavity that pivotally receives the distal ball of the first link. The second link may include a distal ball that is pivotally received within the second drive shaft.

In another aspect of the present disclosure, an adapter includes a proximal portion, an elongate portion, and a distal portion. The proximal portion is configured to couple to a handle. The elongate portion extends from the proximal portion and defines a first longitudinal axis. The distal portion is supported by the elongate portion and is configured to releasably couple a tool assembly to the handle. The distal portion includes a joint assembly including a first support, a second support, a first drive shaft, a second drive shaft, a first link and a spring cage. The first support is disposed along the first longitudinal axis and the second support defines a second longitudinal axis. The first drive shaft is rotatably disposed along the first longitudinal axis and extends through the first support. The second drive shaft is rotatably disposed along the second longitudinal axis and extends through the second support. The first link is disposed between and is coupled to each of the first and second drive shafts such that the first link rotates in response to rotation of the first drive shaft and the second drive shaft rotates in response to rotation of the first link. The spring cage has a first end that is fixed to the first support and a second end that is fixed to the second support. The spring cage defines a spring channel between the first and second supports such that the first link and a portion of the first and second drive shafts are disposed within the spring channel. The spring cage engages the first link to effect uniform articulation across the joint assembly in response to articulation of the second support relative to the first support.

In another aspect of the present disclosure, a surgical system includes a handle, an adapter, and a tool assembly. The adapter is removably coupled to the handle and includes a proximal portion, an elongate portion, and a distal portion. The proximal portion is removably coupled to the handle. The elongate portion extends from the proximal portion and defines a first longitudinal axis. The distal portion is supported by the elongate portion and is configured to releasably couple a tool assembly to the handle. The distal portion includes a joint assembly including a first support, a second support, a first drive shaft, a second drive shaft, a first link and a spring cage. The first support is disposed along the first longitudinal axis and the second support defines a second longitudinal axis. The first drive shaft is rotatably disposed along the first longitudinal axis and extends through the first support. The second drive shaft is rotatably disposed along the second longitudinal axis and extends through the second support. The first link is disposed between and is coupled to each of the first and second drive shafts such that the first link rotates in response to rotation of the first drive shaft and the second drive shaft rotates in response to rotation of the first link. The spring cage has a first end that is fixed to the first support and a second end that is fixed to the second support. The spring cage defines a spring channel between the first and second supports such that the first link and a portion of the first and second drive shafts are disposed within the spring channel. The spring cage engages the first link to effect uniform articulation across the joint assembly in response to articulation of the second support relative to the first support. The tool assembly removably coupled to the distal portion of the adapter.

In another aspect, a joint assembly includes a first support, a second support, a spring cage, a first drive shaft, a second drive shaft, a first cable, and a second cable. The first support defines a first longitudinal axis and the second support defines a second longitudinal axis. The spring cage has a first end that is fixed to the first support and a second end that is fixed to the second support. The spring cage defines a spring channel that extends between the first and second supports. The spring cage urges the first and second supports towards an aligned position in which the first and second longitudinal axes are coaxially aligned. The first drive shaft is rotatably disposed along the first longitudinal axis and extends through the first support and into the spring channel. The second drive shaft is rotatably disposed along the second longitudinal axis and extends through the second support and into the spring channel. The second drive shaft is coupled to the first drive shaft such that the second drive shaft rotates in response to rotation of the first drive shaft. The first and second cables extend through the first support and each has an end secured to the second support. The first and second cables are translatable in a direction parallel to the first longitudinal axis to articulate the second support relative to the first support such that the second longitudinal axis is disposed at a total joint angle relative to the first longitudinal axis.

In aspects, the joint assembly further includes a first link that is disposed within the spring channel and that is coupled to each of the first and second drive shafts such that the first link rotates in response to rotation of the first drive shaft and the second drive shaft rotates in response to rotation of the first link. The first link may define a cavity that pivotally receives a portion of the first drive shaft. The first link may include a distal ball that is coupled to the second drive shaft such that the second drive shaft rotates in response to rotation of the distal ball of the first link. The first link may define a first link axis that is coaxial with the first and second longitudinal exes in the aligned position. The spring cage may control the first link in response to articulation of the second support relative to the first support such that the first link axis defines a first joint angle relative to the first longitudinal axis.

In some aspects, the joint assembly includes a link guide that is disposed about the first link. The link guide may be directly engaged by the spring cage during articulation of the second support in relation to the first support. The link guide may include an inner collar and an outer collar. The inner collar may form a split ring which defines a gap. The outer collar may include an inner surface. The outer collar may be received over the ring of the inner collar such that an inner surface of the outer collar engages the ring of the inner collar to reduce the cap to secure the link guide to the first link. The first link may define a disc positioned between the cavity and the distal ball that is disposed orthogonally to the first link axis. The ring of the inner collar may define a groove that receives the disc to longitudinally secure the link guide relative to the first link.

In particular aspects, the inner collar is formed of a resilient material. The inner collar may be biased outwardly such that engagement between the ring of the inner collar and the inner surface of the outer collar fixes the inner and outer collars relative to one another. The inner collar may be formed of a plastic and the outer collar may be formed of a metal. Alternatively, the inner and outer collars may be formed of a plastic. An outer surface of the outer collar may include a friction reducing coating.

In certain aspects, the joint assembly includes a second link that is disposed within the spring channel. The second link may define a cavity that pivotally receives the distal ball of the first link and may include a distal ball that is pivotally received within the second drive shaft. Rotation of the first link may cause rotation of the second link to cause rotation of the second drive shaft. The second link may define a second link axis that is coaxially aligned with the first and second longitudinal axes in the aligned position. The spring cage may engage the second link during articulation of the second support relative to the first support to provide a uniform articulation along the joint assembly.

In aspects, the first, second, and third joint angles are equal to one another during articulation of the second support relative to the first support. The total joint angle may be the sum of the first, second, and third joint angles during articulation of the second support relative to the first support.

In some aspects, the first and second cables are disposed along an outer surface of the spring cage.

In another aspect of the present disclosure, an adapter includes a proximal portion, and elongate portion, and a distal portion. The proximal portion is configured to couple to a handle. The elongate portion extends from the proximal portion and defines a first longitudinal axis. The distal portion is supported by the elongate portion and is configured to releasably couple a tool assembly to the handle. The distal portion includes a joint assembly having a first support, a second support, a spring cage, a first drive shaft, a second drive shaft, a first cable, and a second cable. The first support is disposed along the first longitudinal axis and the second support defines a second longitudinal axis. The spring cage has a first end that is fixed to the first support and a second end that is fixed to the second support. The spring cage defines a spring channel that extends between the first and second supports. The spring cage urges the first and second supports towards an aligned position in which the first and second longitudinal axes are coaxially aligned. The first drive shaft is rotatably disposed along the first longitudinal axis and extends through the first support and into the spring channel. The second drive shaft is rotatably disposed along the second longitudinal axis and extends through the second support and into the spring channel. The second drive shaft is coupled to the first drive shaft such that the second drive shaft rotates in response to rotation of the first drive shaft. The first and second cables extend from the proximal portion through the first support and each have and end secured to the second support. The first and second cables are translatable in a direction parallel to the first longitudinal axis to articulate the second support relative to the first support such that the second longitudinal axis is disposed at a total joint angle relative to the first longitudinal axis.

In another aspect of the present disclosure, a surgical system includes a handle, an adapter, and a tool assembly. The adapter is removably coupled to the handle and includes a proximal portion, and elongate portion, and a distal portion. The proximal portion is configured to couple to a handle. The elongate portion extends from the proximal portion and defines a first longitudinal axis. The distal portion is supported by the elongate portion and is configured to releasably couple a tool assembly to the handle. The distal portion includes a joint assembly having a first support, a second support, a spring cage, a first drive shaft, a second drive shaft, a first cable, and a second cable. The first support is disposed along the first longitudinal axis and the second support defines a second longitudinal axis. The spring cage has a first end that is fixed to the first support and a second end that is fixed to the second support. The spring cage defines a spring channel that extends between the first and second supports. The spring cage urges the first and second supports towards an aligned position in which the first and second longitudinal axes are coaxially aligned. The first drive shaft is rotatably disposed along the first longitudinal axis and extends through the first support and into the spring channel. The second drive shaft is rotatably disposed along the second longitudinal axis and extends through the second support and into the spring channel. The second drive shaft is coupled to the first drive shaft such that the second drive shaft rotates in response to rotation of the first drive shaft. The first and second cables extend from the proximal portion through the first support and each have and end secured to the second support. The first and second cables are translatable in a direction parallel to the first longitudinal axis to articulate the second support relative to the first support such that the second longitudinal axis is disposed at a total joint angle relative to the first longitudinal axis. The tool assembly is removably coupled to the distal portion of the adapter.

In another aspect of the present disclosure, a joint assembly includes a first support, a second support, a spring cage, a first drive shaft, a second drive shaft, and a first link. The first support defines a first longitudinal axis and the second support defines a second longitudinal axis. The spring cage has a first end fixed to the first support and a second end fixed to the second support. The spring cage defines a spring channel between the first and second supports. The spring cage urges the first and second supports towards an aligned position in which the first and second longitudinal axes are coaxially aligned. The first drive shaft is rotatably disposed along the first longitudinal axis and extends through the first support and into the spring channel. The second drive shaft is rotatably disposed along the second longitudinal axis and extends through the second support and into the spring channel. The second drive shaft is coupled to the first drive shaft such that the second drive shaft rotates in response to rotation of the first drive shaft. The first link is rotatably disposed within the spring channel between and rotatably fixed to the first and second drive shafts. The first link is operably engaged with the spring cage to control an axis of articulation as the second support is articulated relative to the first support.

In another aspect of the present disclosure, a surgical system includes an adapter and a tool assembly. The adapter includes a proximal portion that is configured to releasably couple to a handle and a distal portion that defines a drive axis. The distal portion includes a tool assembly connector having a coupling post that extends in a direction orthogonal to the distal axis. The tool assembly defines a tool axis and includes a coupling mechanism. The coupling mechanism defines a cavity and includes a slider. The cavity is sized and dimensioned to receive the tool assembly connector. The slider is movable in a direction transverse to the tool axis between locked and unlocked positions. The slider defines a locking channel having a locking segment transvers to the tool axis. The slider is configured to receive the coupling post of the adapter in the locking segment when in the locked position to releasably secure the tool assembly to the tool assembly connector.

In aspects, the coupling mechanism defines a cutout that is configured to receive the coupling post of the tool assembly connector when the tool assembly connector is received when the cavity to orient the tool assembly with the distal portion of the adapter. The coupling mechanism includes a blocking section that extends into the cavity and that defines the cutout. The tool assembly connector may include a shelf configured to receive the blocking section when the tool assembly connector is received in the cavity tor rotationally fix the tool assembly and the distal portion of the adapter relative to one another. The coupling post may orthogonally extend form the shelf.

In some aspects, the slider includes a receiving segment that extends in a direction parallel to the tool axis. The receiving segment may be partially defined by a receiving wall that extends over the cutout when the slider is in the locked position. Engagement of the coupling post and the receiving wall may be configured to urge the slider towards an unlocked position until the coupling post is disposed within the locking segment.

In particular aspects, the coupling mechanism includes an alignment post that extends into the cavity. The tool assembly connector may defining an opening configured to receive the alignment post to rotationally fix the tool assembly and the distal portion of the adapter relative to one another. The slider may include a slider post that extends in a direction perpendicular to the tool axis. The coupling mechanism may include a basing member that engages the slider post to bias the slider towards the locked position.

In further aspects, an articulating surgical stapling instrument has a rotatable central drive shaft and at least a first and a second cable. The central drive shaft defines a distal end with a ball. The instrument has an articulation joint has a first link and a second link, each of the first link and the second link having a proximal end with a passage and a distal end with a ball. The ball of the central drive shaft is linked to the ball of the first link, and the ball of the first link is linked to the ball of the second link. The instrument includes a distal drive shaft having a proximal end configured to receive the ball of the second link, the distal drive shaft being linked to the second link. A spring cage surrounds the articulation joint and is attached to a distal housing. The first and the second cables are attached to the distal housing so that movement of the first cable and second cable in opposite directions articulates the distal housing. In certain embodiments, the articulating stapling instrument is powered by a hand held motorized handle, or is embodied as a stapling reload unit that is configured to be used in a robotic surgical system. Also, certain embodiments include a stapling reload that connects to an adapter, the adapter being configured to be connected to the motorized handle, robotic system or a manually operated handle.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 1 is a perspective view of an electromechanical system provided in accordance with the present disclosure;

FIG. 2 is a perspective view of an adapter and a tool assembly of the electromechanical system of FIG. 1 with the tool assembly in an unclamped configuration;

FIG. 3 is an enlarged view of the indicated area of detail of FIG. 2 with a joint assembly of the adapter in an aligned position;

FIG. 4 is an enlarged view of the indicated area of detail of FIG. 3 with a flexible boot of the joint assembly removed;

FIG. 7 is a cross-sectional view taken along section line 7-7 of FIG. 6;

FIG. 8 is a cross-sectional view of the tool assembly and adapter of FIG. 6 during coupling of the tool assembly and the adapter with a distal portion of the adapter partially received within a proximal portion of the tool assembly and a locking mechanism in an unlocked position;

DETAILED DESCRIPTION

Figure 5:
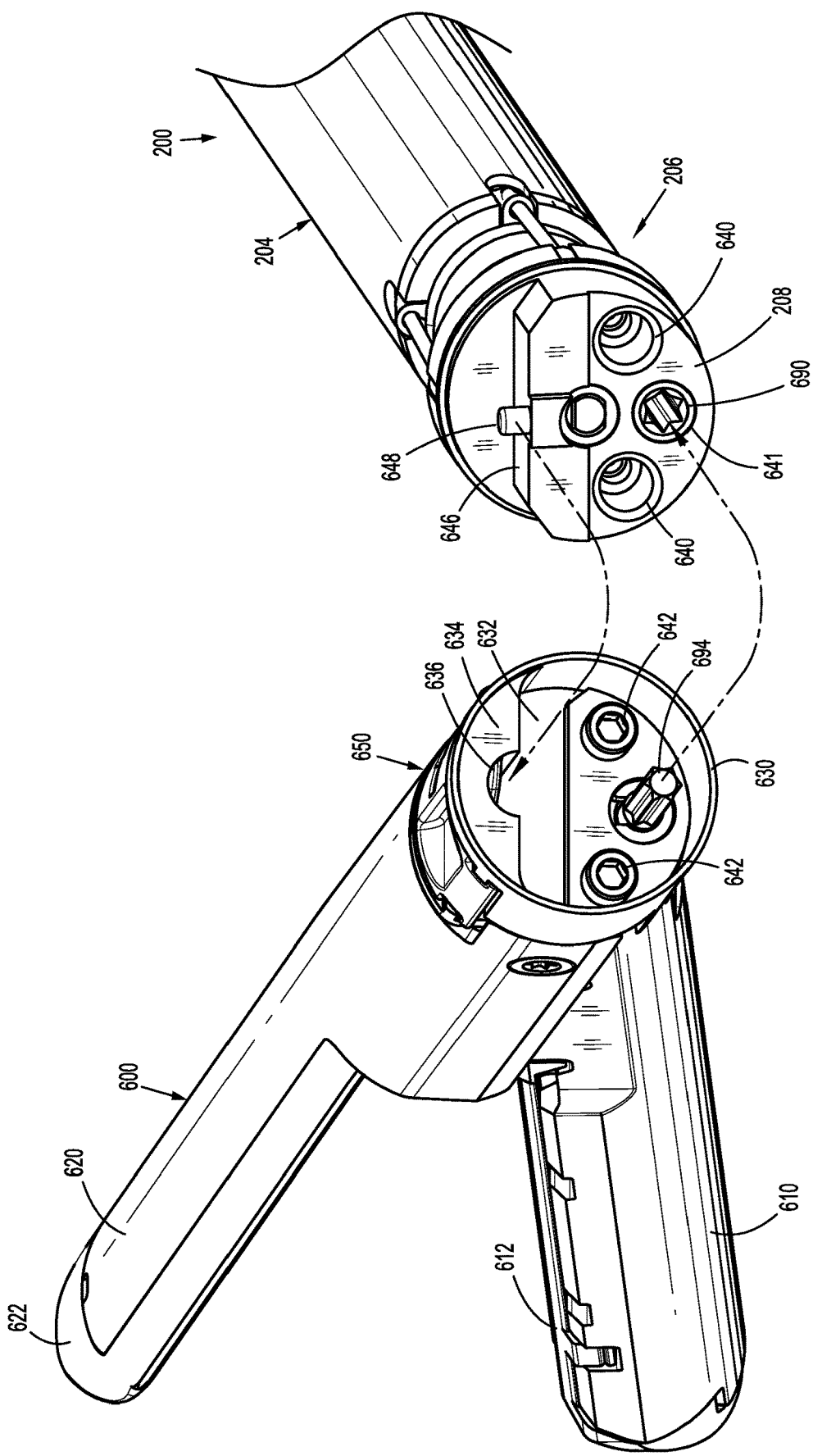
FIG. 5 is a perspective view of a proximal end of the tool assembly and a distal end of the adapter of FIG. 2 with the tool assembly separated from the adapter and the flexible boot removed.
Figure 6:
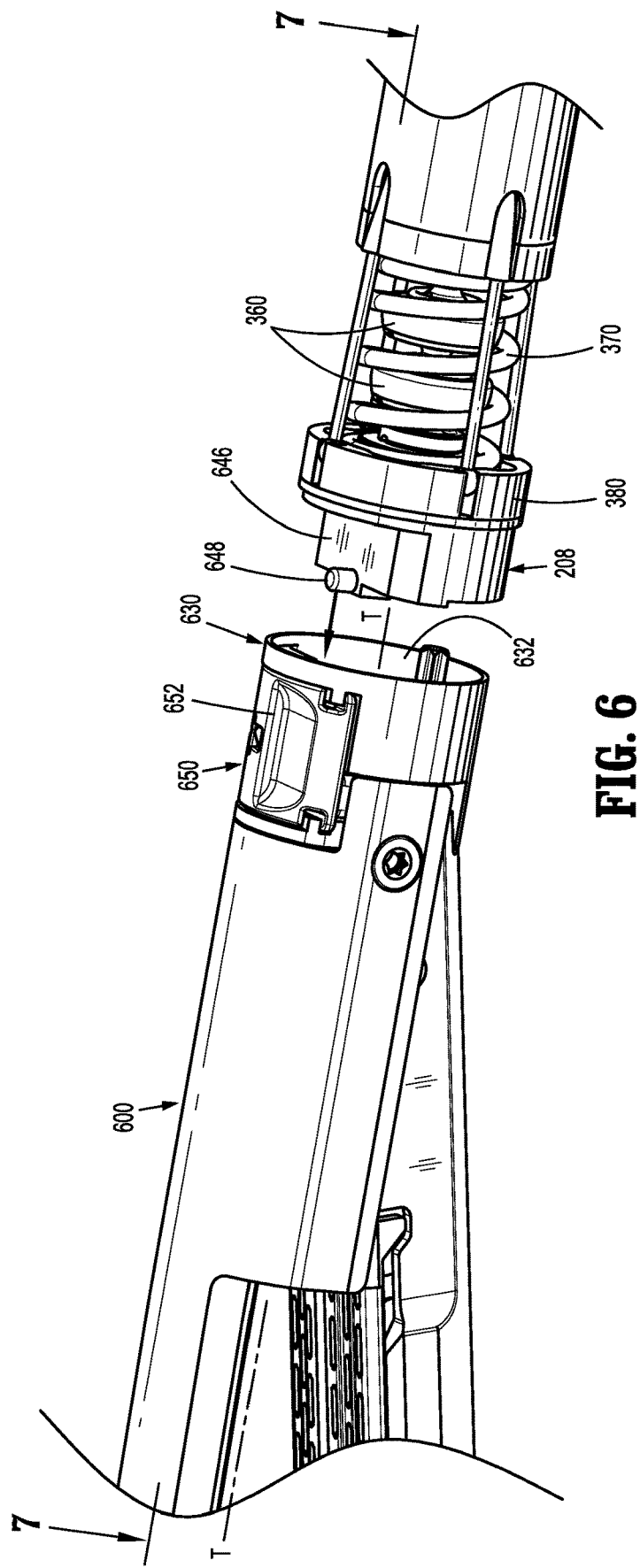
FIG. 6 is a perspective view of the tool assembly of FIG. 5 aligned and oriented with the distal end of the adapter of FIG. 5 prior to coupling of the tool assembly with the adapter.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. In addition, the term "proximal" refers to that portion of the device or component thereof that is closest to the clinician and the term "distal" refers to the portion of that device or component thereof that is farthest from the clinician. Further, in the drawings and in the description that follows, terms such as "front", "rear", "upper", "lower", "top", "bottom" and the like are used simply for convenience of description and are not intended to limit the disclosure thereto.

This disclosure relates generally to an adapter for use with electromechanical surgical systems. The adapter includes a joint assembly including one or more universal joints in the form of links, a spring cage disposed about the universal joints, and proximal and distal supports. The spring cage is supported and extends between the proximal and distal supports. The spring cage and the links cooperate to affect uniform articulation between the proximal and distal supports when the distal support is articulated relative to the proximal support such that each link is articulated to define a similar angle of articulation with adjacent links.

In addition, this disclosure relates to a coupling mechanism for releasably coupling a tool assembly to a distal portion of an adapter. The coupling mechanism includes a slider that moves in a direction transverse to a tool axis of the tool assembly. The distal portion of the adapter includes a coupling post that is captured by the slider in a snap lock manner to releasably secure the tool assembly to the distal portion of the adapter.

Referring now to FIG. 1, a surgical system 10 in accordance with the present disclosure includes a handle 100, an adapter 200, and a tool assembly 600 (e.g., an end effector, multiple- or single-use tool assembly). The handle 100 is configured for releasable connection with the adapter 200, and, in turn, the adapter 200 is configured for releasable connection with the tool assembly 600. Together, the handle 100 and the adapter 200 may cooperate to actuate the tool assembly 600. The surgical system 10 may be an electromechanically powered system and the handle 100 may be electrically powered, e.g., battery powered. Alternatively, the surgical system 10 may be manually actuated.

The handle 100 includes a drive mechanism (not shown) that is configured to drive shafts and/or gear components to perform various operations of the electromechanical surgical system 10. In particular, the drive mechanism is configured to rotate a central drive shaft 260 (FIG. 18), a first link 330 (FIG. 18), and a second link 340 (FIG. 18) to actuate the tool assembly 600 and to manipulate articulation cables 402-408 (FIG. 17) to articulate the tool assembly 600 relative to a longitudinal adapter axis A-A (FIG. 2) of the adapter 200 as described in detail below. For a detailed description of an exemplary powered handle, reference may be made to U.S. Patent Publication No. 2015/0272577 and U.S. Pat. No. 9,055,943. The entire contents of each of these disclosures are incorporated by reference herein.

With additional reference to FIGS. 2-4, the adapter 200 includes a proximal portion 202 (FIG. 2) an elongate portion 204, a distal portion 206, and a tool assembly connector 208. The proximal portion 202 is configured to couple the adapter 200 to the handle 100 (FIG. 1). The elongate portion 204 extends from the proximal portion 202 of the adapter 200 to the distal portion 206 of the adapter 200 and defines the adapter axis A-A of the adapter 200. The distal portion 206 includes a joint assembly 300 that supports the tool assembly connector 208. The tool assembly connector 208 is positioned at a distal end of the distal portion 206 and is configured to couple the tool assembly 600 to the adapter 200. The joint assembly 300 is configured to articulate the tool assembly connector 208 relative to the adapter axis A-A, as described in detail below, to articulate the tool assembly 600 which is supported on the tool assembly connector 208 from a non-articulated position in which a tool axis T-T (FIG. 7) of the tool assembly 600 is aligned with the adapter axis A-A of the adapter 200 to an articulated position in which the tool axis T-T of the tool assembly 600 is misaligned with the adapter axis A-A.

With particular reference to FIGS. 3 and 4, the tool assembly 600 includes a first jaw member 610 and a second jaw member 620 that are movable relative to one another between an open configuration (FIG. 3) and a closed or clamped configuration (not shown). As described in detail below, the joint assembly 300 allows for manipulation of the tool assembly 600 between a non-articulated position and a plurality of articulated positions. In embodiments, the tool assembly 600 is configured as a stapler with the first jaw member 610 releasably receiving a staple cartridge 612 having a plurality of staples or fasteners (not shown) and the second jaw 620 supporting an anvil 622. The staple cartridge 612 may include a shipping wedge 614 that is releasably secured to the staple cartridge 612 to retain the plurality of staples within the staple cartridge 612 during transport. The shipping wedge 614 may also include a tongue 616 that aids in separating the staple cartridge 612 from the first jaw member 610 after use. Exemplary embodiments of a staple cartridge and a shipping wedge are disclosed in commonly owned U.S. Patent Publication No. 2014/0252065, the entire contents of which are hereby incorporated by reference.

Referring to FIGS. 5-11, the tool assembly 600 includes a coupling mechanism 630 to releasably couple the tool assembly 600 to the tool assembly connector 208 of the adapter 200. When the tool assembly 600 is coupled to the tool assembly connector 208, the tool assembly 600 is rotatably and axially fixed to the tool assembly connector 208 of the adapter 200. As such, the tool assembly 600 articulates and rotates relative to the proximal portion 202 (FIG. 2) of the adapter 200 in response to articulation and rotation of the tool assembly connector 208. In addition, when the tool assembly 600 is coupled to the tool assembly connector 208, a drive output 690 of the adapter 200 is engaged with a drive member 694 of the tool assembly 600 such that the drive member 694 of the tool assembly 200 rotates in response to rotation of the drive output 690.

With particular reference to FIG. 5, the tool assembly connector 208 has a distal facing surface that defines openings 640, 641, and includes a shelf 646 with a coupling post 648 extending from the shelf 646 in a direction orthogonal to the shelf 646. The opening 641 receives the drive member 694 of the tool assembly 600 such that the drive member 694 engages the drive output 690 of the adapter 200.

The coupling mechanism 630 of the tool assembly 600 defines a connector cavity 632 that is sized and dimensioned to mate with the tool assembly connector 208 of the adapter 200 such that the tool assembly connector 208 is at least partially received within the connector cavity 632. It is contemplated that the entire tool assembly connector 208 may be received within the connector cavity 632.

The coupling mechanism 630 includes alignment posts 642 that extend proximally into the connector cavity 632 and are sized and dimensioned to be received within the openings 640 of the tool assembly connector 208 of the adapter 200 to align the tool assembly 600 with the tool assembly connector 208 and to rotatably fix the tool assembly 600 relative to the tool assembly connector 208. The coupling mechanism 630 also includes a blocking section 634 that extends distally into the connector cavity 632 and is sized and dimensioned to engage the shelf 646 of the tool assembly connector 208. Engagement between the blocking section 634 and the shelf 646 rotatably fixes the tool assembly 600 relative to the tool assembly connector 208. The blocking section 634 defines a cutout 636 that is sized and dimensioned to allow the coupling post 648 of the shelf 646 of the tool assembly connector 208 to pass by the blocking section 634 deeper into the connector cavity 632. As shown, the cutout 636 has a semi-cylindrical shape; however, the cutout 636 may have a plurality of shapes, e.g., a rectangular shape.

Figure 9:
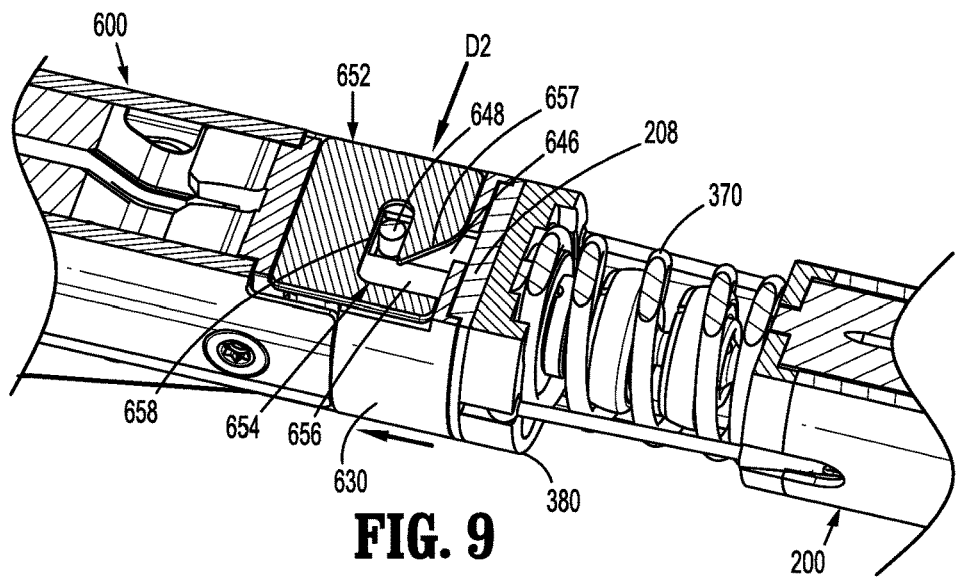
FIG. 9 is a cross-sectional view of the tool assembly and adapter of FIG. 6 with the distal portion of the adapter fully received within the proximal portion of the tool assembly and the locking mechanism in a locked position.
Figure 10:
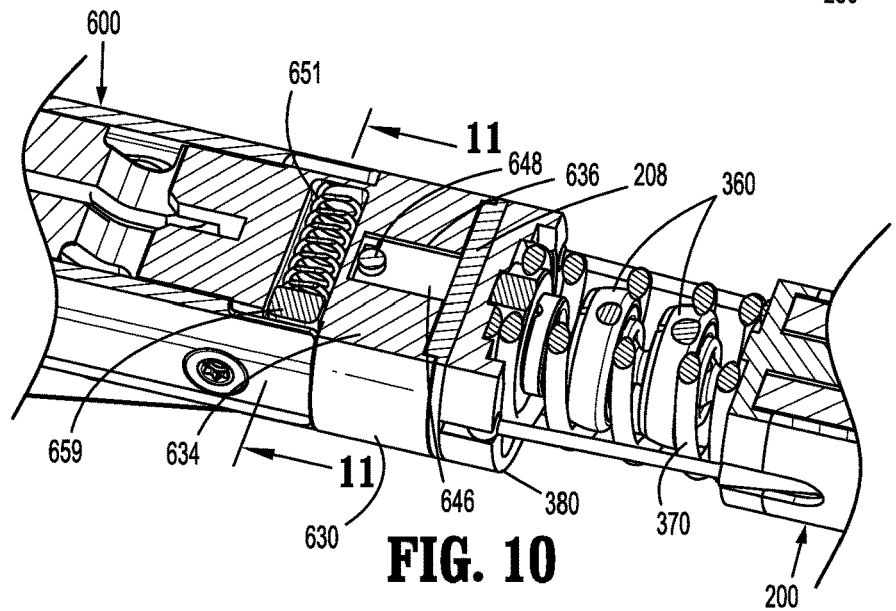
FIG. 10 is a cross-sectional view taken along section line 10-10 of FIG. 4.

Referring now to FIGS. 6-11, the coupling mechanism 630 includes a locking assembly 650 to releasably secure the tool assembly connector 208 within the connector cavity 632. The locking assembly 650 includes a slider 652 and a biasing member 651 (FIG. 10). As detailed below, the slider 652 is movable in a direction transverse to the tool axis T-T between a locked position and an unlocked position to receive and releasably secure the tool assembly connector 208 within the connector cavity 632.

With particular reference to FIG. 7, the slider 652 defines a locking channel 654 that is parallel to and laterally offset from the tool axis T-T. The locking channel 654 has a receiving segment 656 and a locking segment 658 that receives the coupling post 648 of the tool assembly connector 208. As shown, the receiving segment 656 defines an axis that is substantially parallel to the tool axis T-T and the locking segment 658 defines an axis that is substantially perpendicular to the tool axis T-T and the axis of the receiving segment 656. When the tool assembly connector 208 is received within the connector cavity 632, the tool assembly connector 208 is longitudinally fixed relative to the tool assembly 600. The receiving segment 656 is partially defined by a receiving wall 657 that is disposed at an angle relative to the tool axis T-T and is positioned over the cutout 636 when the slider 652 is in the locked configuration as shown in FIG. 7.

In embodiments, the locking segment 658 of the locking channel 654 can define an angle less than or greater than 90° with the receiving segment 656. In embodiments where the locking segment 658 defines an angle greater than 90° with the receiving segment 656, the biasing member 651 (FIG. 10) may cause the locking mechanism 650 to draw the tool assembly connector 208 further into the connector cavity 632 as the slider 652 engages the coupling post 648 and returns to the locked position. In embodiments where the locking segment 658 defines an angle less than 90° with the receiving segment 656, the biasing member 651 (FIG. 10) may cause the locking mechanism 650 to urge the tool assembly connector 208 out of the connector cavity.

Figure 11:
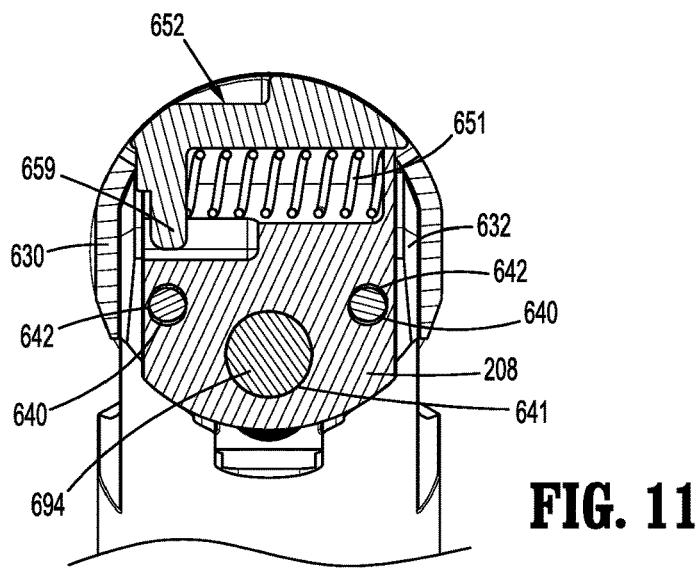
FIG. 11 is a cross-sectional view taken along section line 11-11 of FIG. 10.

With particular reference to FIGS. 10 and 11, the biasing member 651 is disposed within the coupling mechanism 630 and is compressible in a direction transverse to the longitudinal axis T-T of the tool assembly 600. The biasing member 651 is engaged with a slider post 659 of the slider 652 to urge the slider 652 transversely towards the locked position. The slider post 659 extends from the slider 652 in a direction perpendicular to the tool axis.

Referring to FIGS. 7-10, the releasable coupling of the tool assembly connector 208 of the adapter 200 in the connector cavity 632 of the coupling mechanism 630 is described in detail. Initially referring to FIG. 7, the tool assembly 600 is aligned and oriented with the adapter 200 such that the tool axis T-T is aligned with the adapter axis A-A and the coupling post 648 is oriented to pass into the cutout 636. When the tool assembly 600 is aligned with and oriented with the adapter 200, the tool assembly connector 208 is moved into the connector cavity 632 in a direction parallel to the tool axis T-T as represented by the arrow C.

With reference to FIG. 8, when the tool assembly connector 208 enters the connector cavity 632, the coupling post 648 enters the cutout 636 of the coupling mechanism 650. Engagement between the coupling post 648 and walls of the blocking segment 634 defining the cutout 636 may rotate the tool assembly 600 about the tool axis T-T to finely orient the tool assembly 600 relative to the adapter 200. As the coupling post 648 passes through the cutout 636, the coupling post 648 engages the receiving wall 657 of the slider 652 that defines a portion of the receiving segment 656. Engagement between the coupling post 648 and the receiving wall 657 forces the slider 652 to move in a first direction, as represented by arrow D1, towards the unlocked position against the bias of the biasing member 651. More specifically, as the slider 652 moves in the first direction, the slider post 659 (FIG. 11) of the slider 652 compresses the biasing member 651.

Referring to FIGS. 9 and 10, when the tool assembly connector 208 is received within the connector cavity 632, the coupling post 648 is moved past the receiving wall 657 defining the receiving segment 656 and into the locking segment 658. As the coupling post 648 enters the locking segment 658, the biasing member 651 urges the slider post 659 to move the slider 652 in a second direction opposite the first direction, represented by arrow D2, to return the slider 652 to the locked position. When the slider 652 is in the locked position with the coupling post 648 positioned within the locking segment 658, the tool assembly connector 208 is secured within the connector cavity 630 to secure the tool assembly 600 to the adapter 200. When the tool assembly 600 is secured to the adapter 200, the alignment posts 642 (FIG. 11) of the coupling mechanism 630 are received within the openings 640 of the tool assembly connector 208 to fixedly retain the orientation of the tool assembly 600 relative to the tool assembly connector 208 as shown in FIG. 11.

To release the tool assembly 600 from the adapter 200, the slider 652 is moved to the unlocked position and the adapter 200 is moved away from the tool assembly 600. When the slider 652 is in the unlocked configuration, the coupling post 648 is aligned with the receiving segment 656 of the locking channel 654 such that the tool assembly 600 can be manually separated from the adapter 200. When the tool assembly 600 is separated from the adapter 200, the slider 652 can be released to allow the biasing member 651 to return the slider 652 to the locked configuration.

Figure 12:
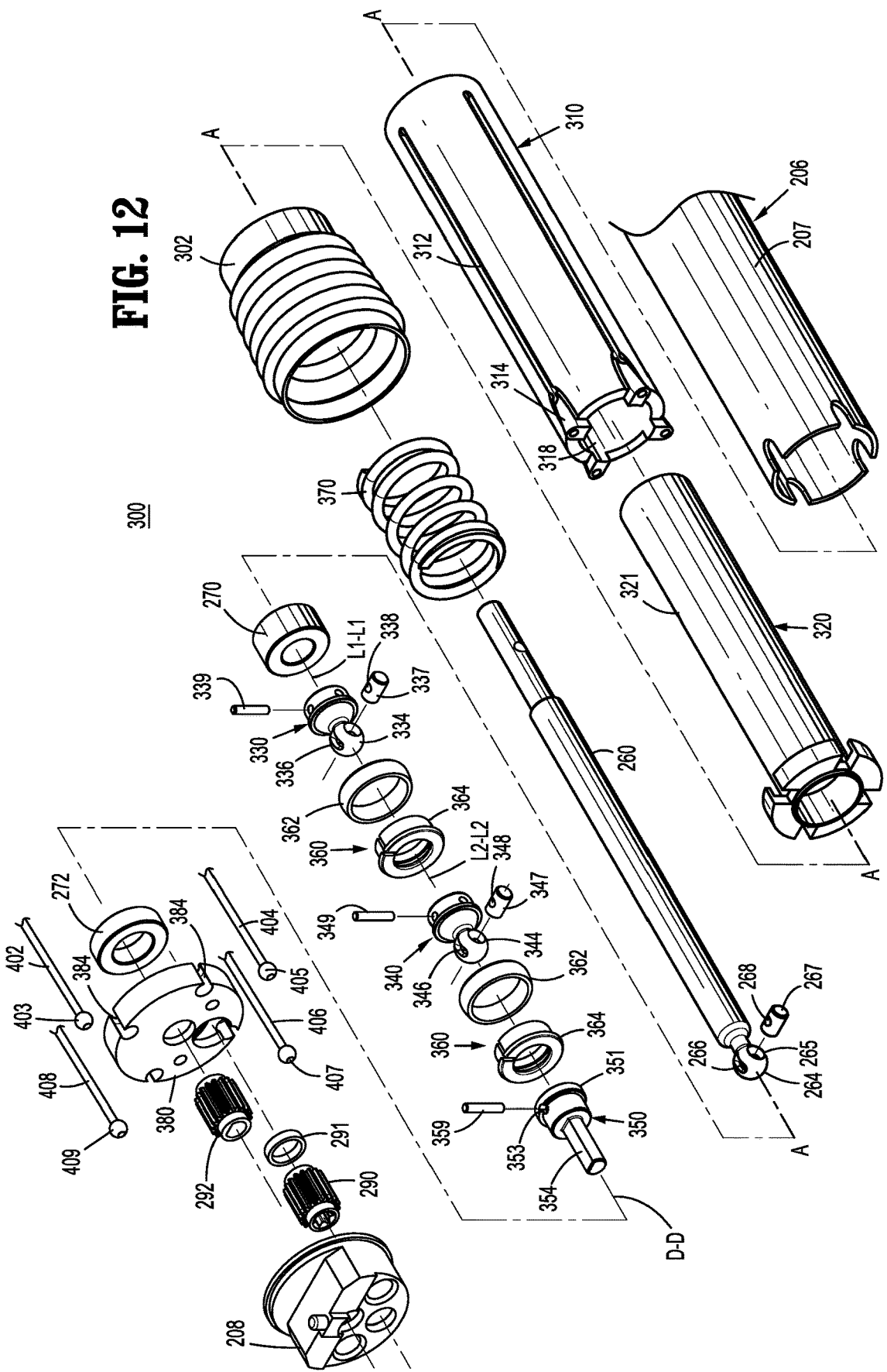
FIG. 12 is a perspective view, with parts separated, of a distal portion of the adapter of FIG. 2.

Referring to FIG. 12, the joint assembly 300 is disposed in the distal portion 206 of the adapter 200 and is configured to control articulation of the tool assembly connector 208 relative to the distal portion 206 such that articulation of the tool assembly 600 is predictable and stable during all phases of operation of the surgical system 10. The joint assembly 300 includes a flexible boot 302, a cable guide 310, a proximal support 320, a first link 330, a second link 340, a distal drive shaft 350, link guides 360, a spring cage 370, and a distal support 380.

Figure 13:
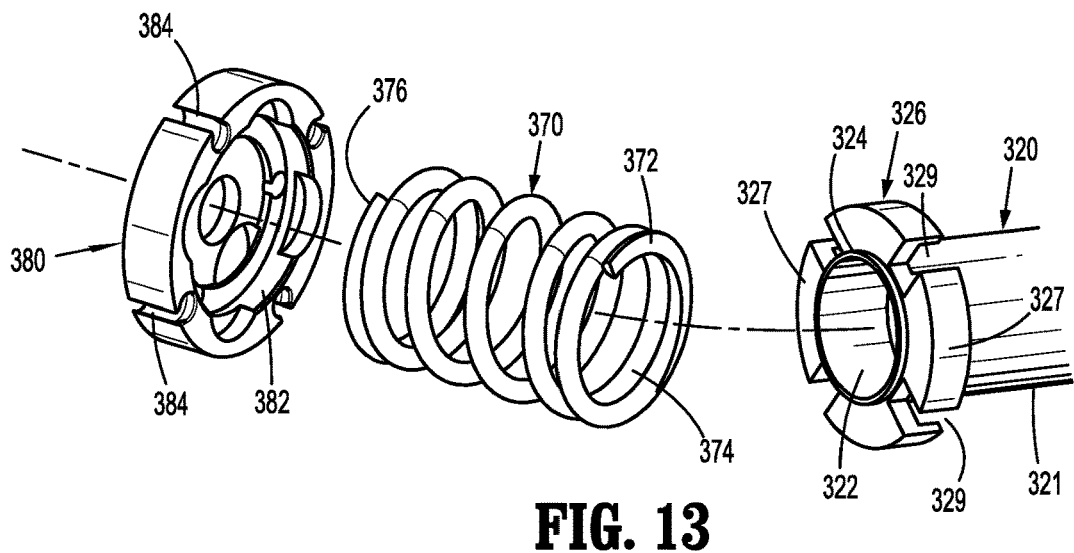
FIG. 13 is an enlarged view of a proximal support, a spring cage, and a distal support of the joint assembly of FIG. 12 with parts separated from one another.
Figure 14:
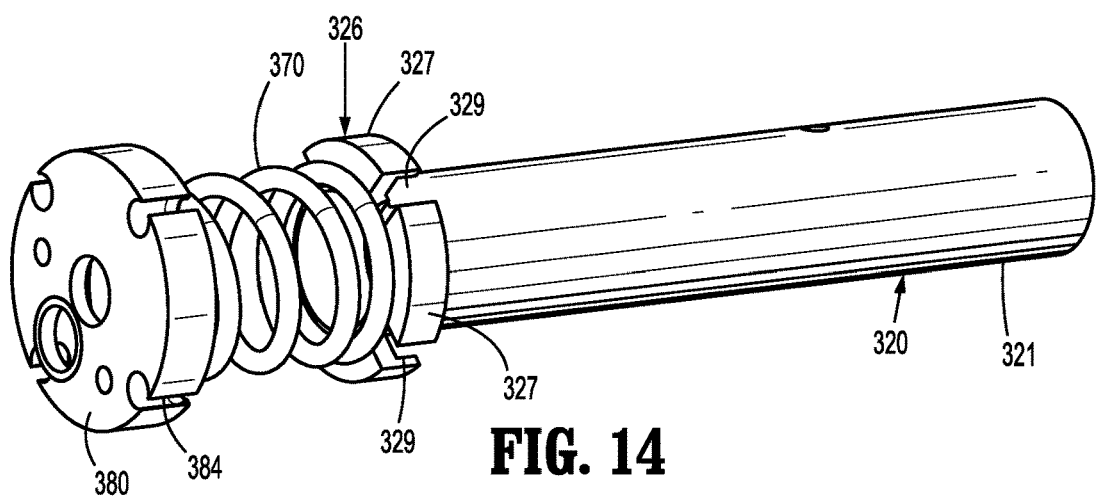
FIG. 14 is a side perspective view from the distal end of the proximal support, the spring cage, and the distal support of the joint assembly of FIG. 13 assembled with one another.
Figure 15:
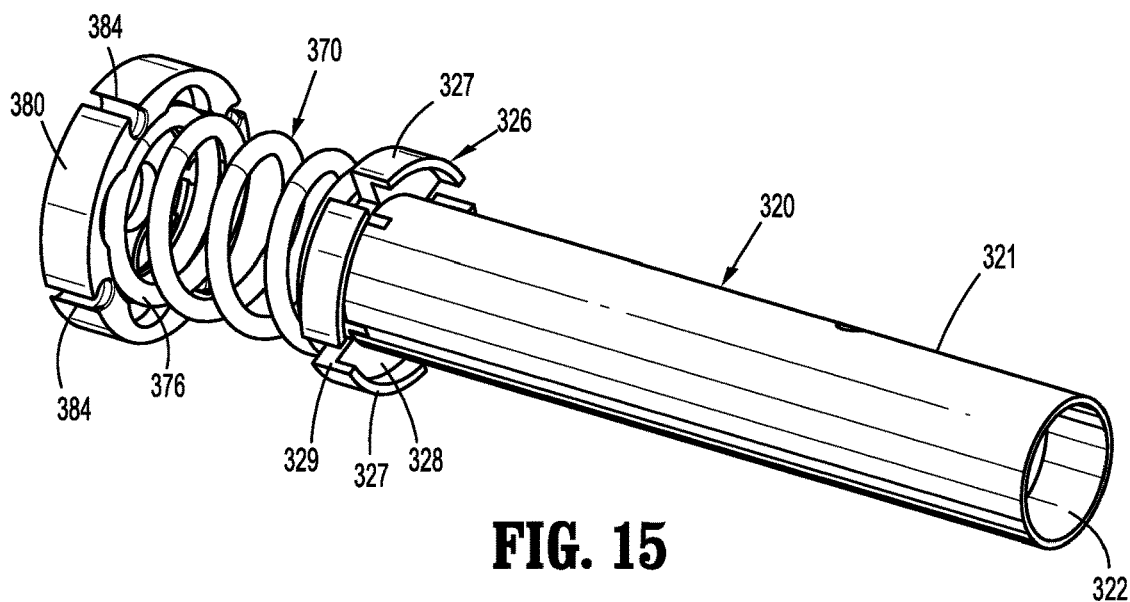
FIG. 15 is a side perspective view from the proximal end of the proximal support, the spring cage, and the distal support of the joint assembly of FIG. 13 assembled with one another.

With additional reference to FIGS. 13-15, the proximal support 320 is substantially cylindrical and defines a central passage 322 therethrough. The proximal support 320 includes a cylindrical portion 321 and a distal flange 326. The cylindrical portion 321 of the proximal support 320 is received within the cable guide 310 such that the central passage 322 is coaxial with the adapter axis A-A of the adapter 200. The distal flange 326 includes wings 327 that extend radially outward from the cylindrical portion 321 and cooperate with the cylindrical portion 321 to define proximally facing recesses 328 and slots 329 between adjacent wings 327. The proximally facing recess 328 and each of the slots 329 receive portions of the cable guide 310 (FIG. 12) as detailed below. A portion of the cylindrical portion 321 extends distally beyond the distal flange 326 to define a race 324 (FIG. 13).

The spring cage 370 includes a proximal end 372 and a distal end 376 and defines a spring channel 374 that extends between the proximal and distal ends 372, 376. The proximal end 372 of the spring cage 370 is secured to the proximal support 320 such that the spring channel 374 is in communication with the central passage 322. The race 324 is received within the spring channel 374 to coaxially align the proximal end 372 of the spring cage 370 with the proximal support 320. The proximal end 372 may be welded to the wings 327 and/or the cylindrical portion 321 of the proximal support 320.

The distal support 380 is secured to the distal end 376 of the spring cage 370. Specifically, the distal support 380 defines a proximally facing socket 382 that receives the distal end 376 of the spring cage 370 such that the distal end of the spring cage 370 moves in unison with the distal support 380. The distal end 376 may be welded within the socket 382. The distal support 380 also defines openings 384 that receive portions of articulation cables 402-408 (FIG. 17) as detailed below.

Figure 16:
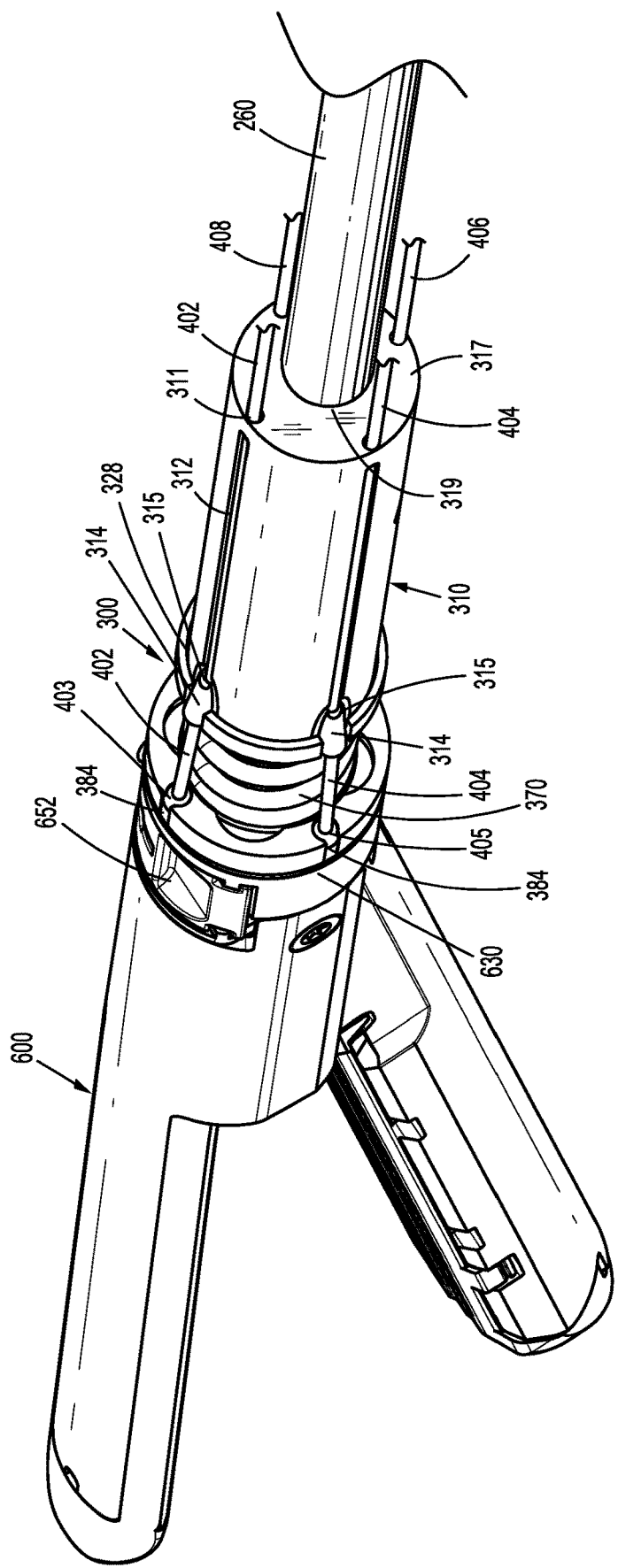
FIG. 16 is a rear perspective view of a distal portion of the adapter and tool assembly of FIG. 2 with an outer tube and the flexible boot of the adapter removed.
Figure 17:
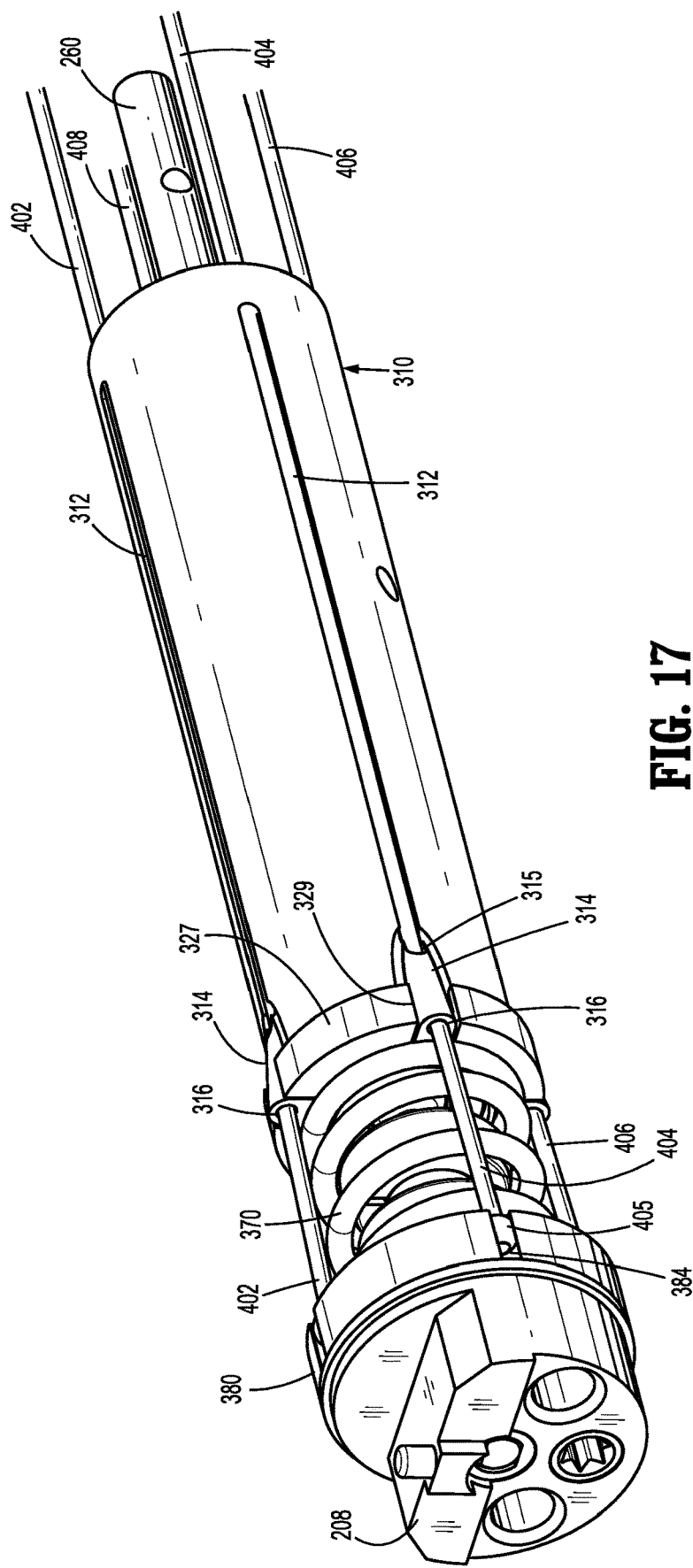
FIG. 17 is a perspective view of a distal portion of the adapter of FIG. 16 with the outer tube and the flexible boot removed.

With reference to FIGS. 16 and 17, the cable guide 310 is supported within the distal portion of the adapter 206 and directs the articulation cables 402-408 of an articulation mechanism 400 around the spring cage 370 towards the distal support 380. The cable guide 310 is substantially tubular and defines a central passage 318 (FIG. 12). The cable guide 310 includes a proximal plate 317 that substantially closes the proximal portion of the cable guide 310. The proximal plate 317 defines a drive shaft opening 319 that receives the central drive shaft 260 and cable openings 311 that are aligned with the cable grooves 312. The cable grooves 312 extend in a direction parallel to the adapter axis A-A and receive and guide movement of the articulation cables 402-408.

With particular reference to FIG. 17, the cable guide 310 includes cable lifts 314, each defining a proximal aperture 315 and a distal aperture 316. Each cable lift 314 receives a respective one of the articulation cables 402-408 from a respective groove 312. Each cable 402-408 extends through the proximal aperture 315, through the distal aperture 316, and towards the distal support 380 such that each of the articulation cables 402-408 is disposed along an outer surface of the spring cage 370 and is secured to the distal support 380. In embodiments, a distal end of each of the articulation cables 402-408 includes a ferrule that is received in an opening 384 formed in the distal support 380. For example, the cable 404 includes a ferrule 405 at the distal end of the cable 404 that is received within a respective one of the openings 384 in the distal support 380. In embodiments, the grooves 312 and the cable lifts 314 are equally spaced about the adapter axis A-A. As shown there are four articulation cables 402-408 and the grooves 312 and the cable lifts 314 are spaced about 90° apart from one another about the cable guide 310. It is contemplated that there may be less than four or greater than four articulation cables.

With reference again to FIGS. 16 and 17, the central passage 318 of the cable guide 310 (FIG. 23) receives the cylindrical portion 321 (FIG. 12) of the proximal support 320. When the cylindrical portion 321 is received within the central passage 318, each of the cable lifts 314 extends through a respective one of the slots 329 defined between the wings 327 of the proximal support 320. In addition, a distal portion of the cable guide 310 is received within the proximally facing recesses 328 (FIG. 16) defined by the wings 327. The distal portion of the cable guide 310 may engage the wings 327 to prevent excessive distal translation of the cable guide 310 over the proximal support 320. A proximal portion of the proximal support 320 may engage the proximal plate 317 of the cable guide 310 to prevent the proximal support 320 from passing entirely through the cable guide 310.

Figure 18:
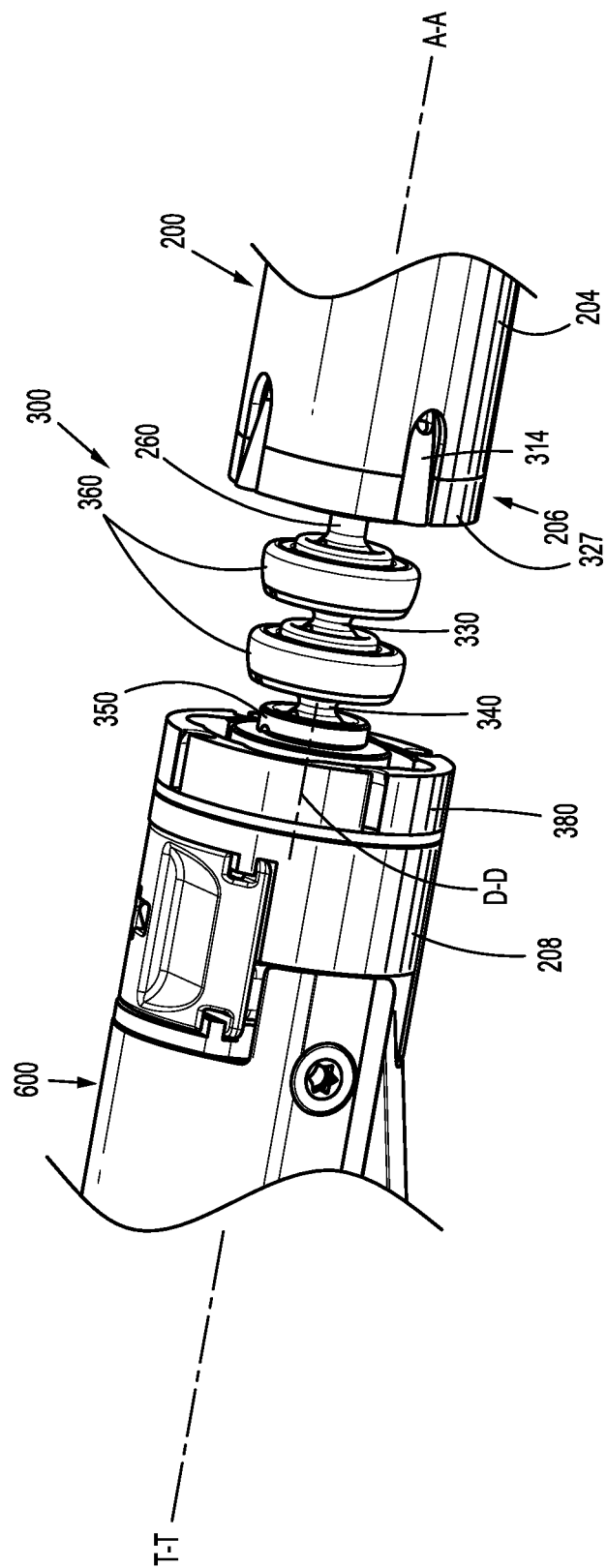
FIG. 18 is a perspective view of the joint assembly of FIG. 6 with the flexible boot, the spring cage, and articulation cables removed.

Referring to FIG. 18, a central drive shaft 260 of the adapter 200 is operably coupled to the distal drive shaft 350 of the joint assembly 300 by the first and second links 330, 340 such that the distal drive shaft 350 rotates in response to rotation of the central drive shaft 260. The central drive shaft 260 is disposed along the adapter axis A-A of the adapter 200 and the distal drive shaft 350 defines a distal drive axis D-D that is parallel to the longitudinal axis T-T of the tool assembly 600 when the tool assembly 600 is coupled to the adapter 200. As detailed below, the distal drive shaft 350 has an aligned position, in which the distal drive axis D-D is aligned with the adapter axis A-A, and a plurality of articulated positions, in which the distal drive axis D-D defines an angle with the adapter axis A-A.

The first and second links 330, 340 are sequentially disposed within the spring cage 370 between the central drive shaft 260 and the distal drive shaft 350 to rotatably couple the distal drive shaft 350 to the central drive shaft 260. With additional reference back to FIG. 12, the central drive shaft 260 includes a drive ball 264 that defines a transverse passage 265 and arced slots 266 that are in communication with the transverse passage 265. The transverse passage 265 passes through the center of the drive ball 264 and extends in a direction orthogonal to the adapter axis A-A. The transverse passage 265 of the drive ball 264 rotatably receives a center pin 267. The center pin 267 defines a pin opening 268 that passes through the middle of the center pin 267 in a direction orthogonal to a central longitudinal axis of the center pin 267. The arced slots 266 of the drive ball 264 are defined in a plane parallel to and passing through the adapter axis A-A.

With reference to FIGS. 19-22, the first link 330 defines a first link axis L1-L1 and includes a proximal ring 331, a distal ball 334, and a central disc 361. The proximal ring 331 defines a proximal cavity 332 that is sized and dimensioned to receive the drive ball 264 (FIG. 12) of the central drive shaft 260. An outer surface of the proximal ring 331 defines pin holes 333 that are aligned about an axis orthogonal to the first link axis L1-L1. The first link 330 includes a drive pin 339 that is received through the pin holes 333, the arced slots 266 (FIG. 12) of the drive ball 264, and the pin opening 268 (FIG. 12) of the center pin 267 to couple the first link 330 to the drive ball 264 of the central drive shaft 260 while permitting the first link 330 to articulate about the central pin 267 in the plane defined by the arced slots 266 (FIG. 12) such that the first link axis L1-L1 can be rotated in relationship to the adapter axis A-A to define an angle with the adapter axis A-A as detailed below.

The arced slots 266 and the drive pin 339 limit the degree of articulation of the first link 330 relative to the central drive shaft 260. Specifically, as the first link 330 articulates about the central pin 267, the drive pin 339 pivots within the arced slots 266 until the drive pin 339 reaches an end of the arced slots 266 to define a maximum angle of articulation between the first link 330 and the central drive shaft 260. The maximum angle of articulation between the first link 330 and the central drive shaft 260 is in a range of about 15° to about 60°, e.g., about 30°. As such, to accommodate an angle of articulation of greater than a maximum angle of articulation of a single joint, additional articulation links are required. For example, if a joint assembly only has two components articulable relative to one another, e.g., the central drive shaft 260 and the distal drive shaft 350, the maximum angle of articulation between two components may be limited to a first angular degree, e.g., 30°. To exceed this first angular degree of articulation, a link, e.g., first link 330, may be positioned between the first two components to double the angular degree of articulation, e.g., 60°, between the first two components, e.g., the central drive shaft 260 and the distal drive shaft 380. Similarly, to exceed this second angular degree of articulation, another link, e.g., second link 340, can be sequentially added to reach a third angular degree of articulation, e.g., 90°. Continuing, it is envisioned that a fourth angular degree of articulation may be achieved, e.g., 120°, by sequentially adding another link between the first two components.

The distal ball 334 of the first link 330 is similar to the drive ball 264 (FIG. 12) of the central drive shaft 260 and defines a transverse passage 335 and arced slots 336 that are in communication with the transverse passage 335. The transverse passage 335 passes through the center of the distal ball 334 and extends in a direction orthogonal to the first link axis L1-L1. The transverse passage 335 of the distal ball 334 rotatably receives a center pin 337. The center pin 337 defines a pin opening 338 that passes through the middle of the center pin 337 in a direction orthogonal to a central longitudinal axis of the center pin 337. The arced slots 336 of the distal ball 334 are defined in a plane parallel to and passing through the first link axis L1-L1.

The link guide 360 is coupled to the first link 330 to position the first link 330 within the spring channel 374 (FIG. 13) of the spring cage 370 and to rotate the first link 330 about the drive ball 264 of the central drive shaft 260 in response to articulation of the spring cage 370 as detailed below. The link guide 360 includes an outer collar 362 and an inner collar 364. The outer collar 362 includes an inner surface 363a that defines a central opening of the outer collar 362 and an outer surface 363b that is configured to engage the spring cage 370 to center the first link 330 within the spring cage 370. The inner collar 364 is in the form of a split ring with a proximal section 365 and a distal flange 367. The proximal section 365 has an inner surface 368 that defines a disc groove 369 that receives the central disc 361 of the first link 330. The distal flange 367 extends beyond an outer surface of the proximal section 365 a distance approximately equal to a thickness of the outer collar 362 defined between the inner and outer surfaces 363a, 363b.

Figure 19:
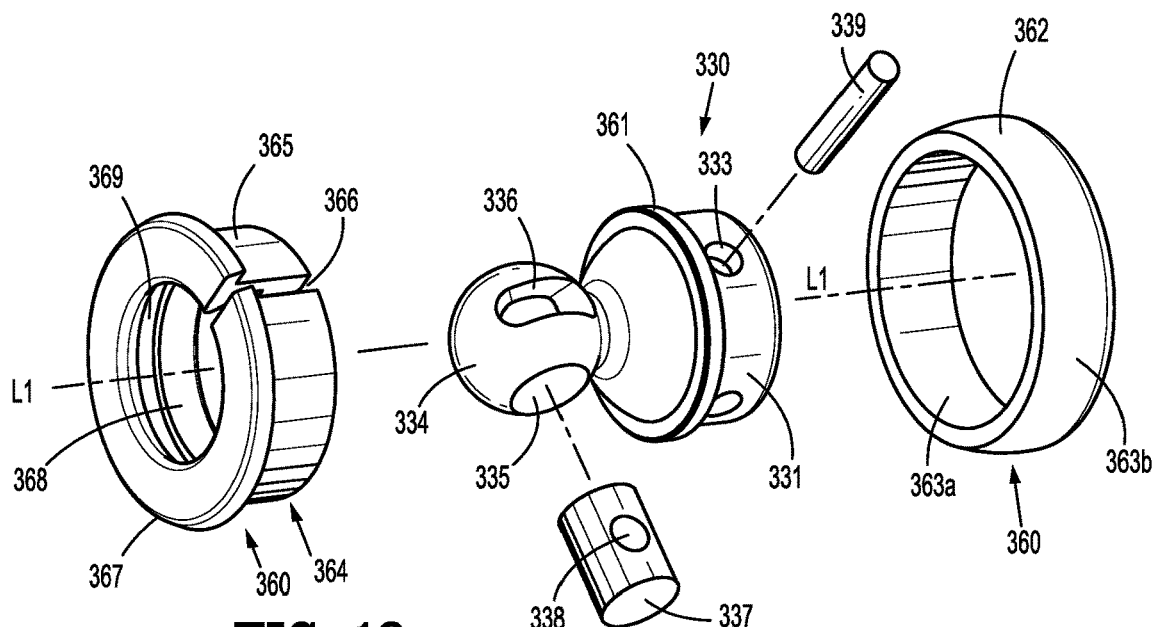
FIG. 19 is a perspective view of a first link and a link guide of the distal portion of the adapter of FIG. 12 with parts separated.
Figure 20:
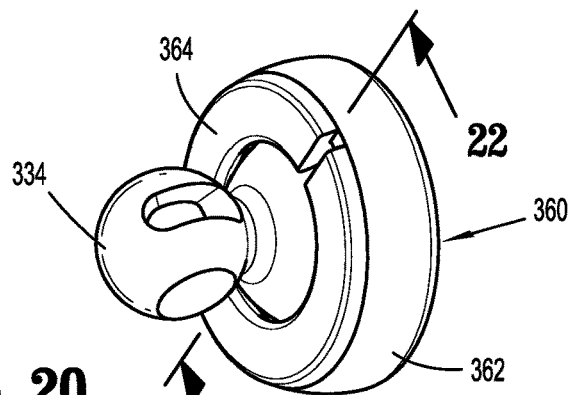
FIG. 20 is a perspective view from the distal end of the first link and the link guide of FIG. 19 assembled with one another.
Figures 21, 22:
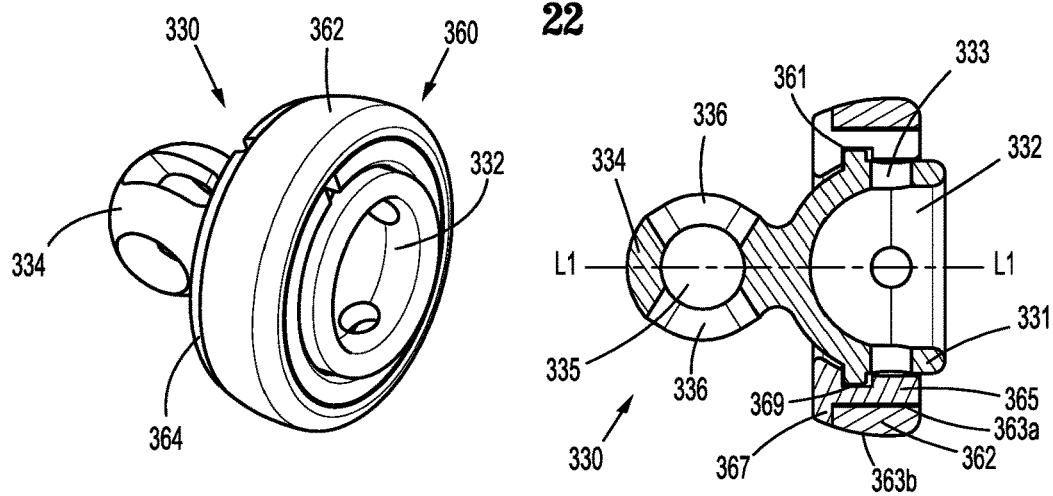
FIG. 21 is a perspective view from the proximal end of the first link and the link guide of FIG. 20.
FIG. 22 is a cross-sectional view taken along section line 22-22 of FIG. 20.

With particular reference to FIG. 22, the proximal section 365 of the inner collar 364 is positioned over the first link 330 with the central disc 361 of the first link 330 received within the disc groove 369 of the link guide 360. The split 366 in the inner collar 364 allows the inner collar 364 to expand such that the central disc 361 of the first link 330 can pass through the proximal section 365 until the central disc 361 is positioned within the disc groove 369. The outer collar 362 is then slid over the proximal section 365 such that the inner surface 363a of the outer collar 362 engages the proximal section 365 to compress the proximal section 365 such that the split 366 is reduced or eliminated and the inner and outer collars 362, 364 are secured to the first link 330. The inner surface 363a and/or the proximal section 365 may have enhanced frictional features to increase resistance to translation between the inner and outer collars 362, 364. In addition, the inner collar 364 may be formed of a resilient material that is self-biased to an expanded configuration such that the split 366 has a first dimension as shown in FIG. 19 in a compressed configuration, and a second dimension less that the first dimension, when the proximal section 365 is urged into engagement with the inner surface 363a of the outer collar 362. When the inner collar 364 is received within the outer collar 362, the distal flange 367 of the inner collar 364 is coincident with an outer surface 363b of the outer collar 362.

In embodiments, the outer collar 362 is formed from a metal and the inner collar 364 is formed from a plastic. Forming the outer collar 362 from metal may reduce distortion or pinching of the link guide 360 as the link guide 360 is engaged by the spring cage 370 as detailed below. Forming the inner collar 364 from a plastic may reduce friction between the inner collar 364 and the first link 330 as the first link 330 rotates relative to the link guide 360 as detailed below. It is contemplated that the inner collar 364 may be formed from a metal with a friction reducing coating to reduce friction between the inner collar 364 and the first link 330. It will be appreciated that reducing friction between the link guide 360 and the first link 330 may reduce generation of heat during rotation of the first link 330 as well as reduce the amount of force required to effect articulation.

In some embodiments, the link guide 360 is formed from a single collar that has sufficient strength to prevent distortion from the spring cage 370 during articulation and has a low surface roughness to reduce friction between the inner collar 364 and the first link 330. In these embodiments, it is contemplated that the link guide 360 may be formed of a metal or a plastic.

The construction of the second link 340 is substantially similar to the construction of the first link 330. Accordingly, the construction of the second link 340 will not be described in detail and has like structures represented with similar labels.

Figure 23:
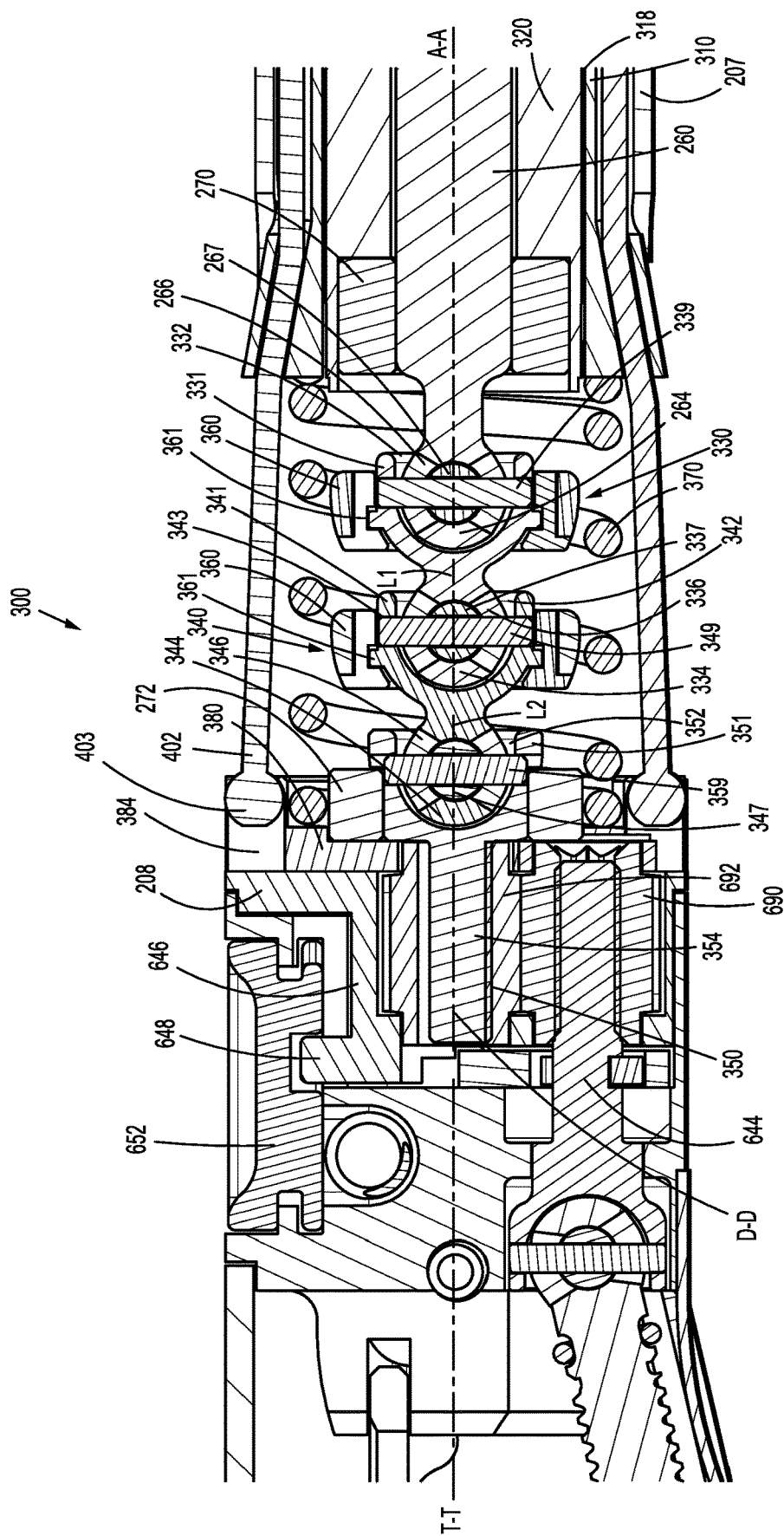
FIG. 23 is a cross-sectional view taken along section line 23-23 of FIG. 4 illustrating the joint assembly in the aligned position.

Referring to FIGS. 12 and 23, the distal drive shaft 350 defines the distal drive axis D-D and includes a proximal ring 351 and a distal shaft 354. The proximal ring 351 defines a proximal cavity 352 (FIG. 23) that receives the distal ball 344 of the second link 340. An outer surface of the proximal ring 351 defines pin holes 353 that are aligned about an axis orthogonal to the distal drive axis D-D. The drive pin 359 is received through the pin holes 353 of the distal drive shaft 350, the arced slots 346 of the second link 340, and the pin opening 348 of the central pin 347 to couple the distal drive shaft 350 to the second link 340 while permitting the distal drive shaft 350 to articulate about the central pin 347 in the plane defined by the arced slots 346 such that the distal drive axis D-D defines an angle with the second link axis L2-L2 as detailed below.

With reference also to FIG. 18, the joint assembly 300 has an aligned position in which the tool assembly 600 is coaxially aligned with the adapter 200 such that the tool axis T-T is coaxial with the adapter axis A-A. In the aligned position, the first link axis L1-L1, the second link axis L2-L2, and the distal drive axis D-D are coaxial with the adapter axis A-A as shown in FIG. 23. The spring cage 370 is engaged with the proximal support 320 and the distal support 380 such that the spring cage 370 exerts an alignment force that urges the proximal and distal supports 320, 380 apart from one another such that the joint assembly 300 is urged to the aligned position. The adapter 200 includes an articulation mechanism 400 (FIG. 26) that maintains the articulation cables 402-408 taut in the aligned position such that each of the articulation cables 402-408 exerts a substantially equal force on the distal support 380 relative to one another.

Figure 24:
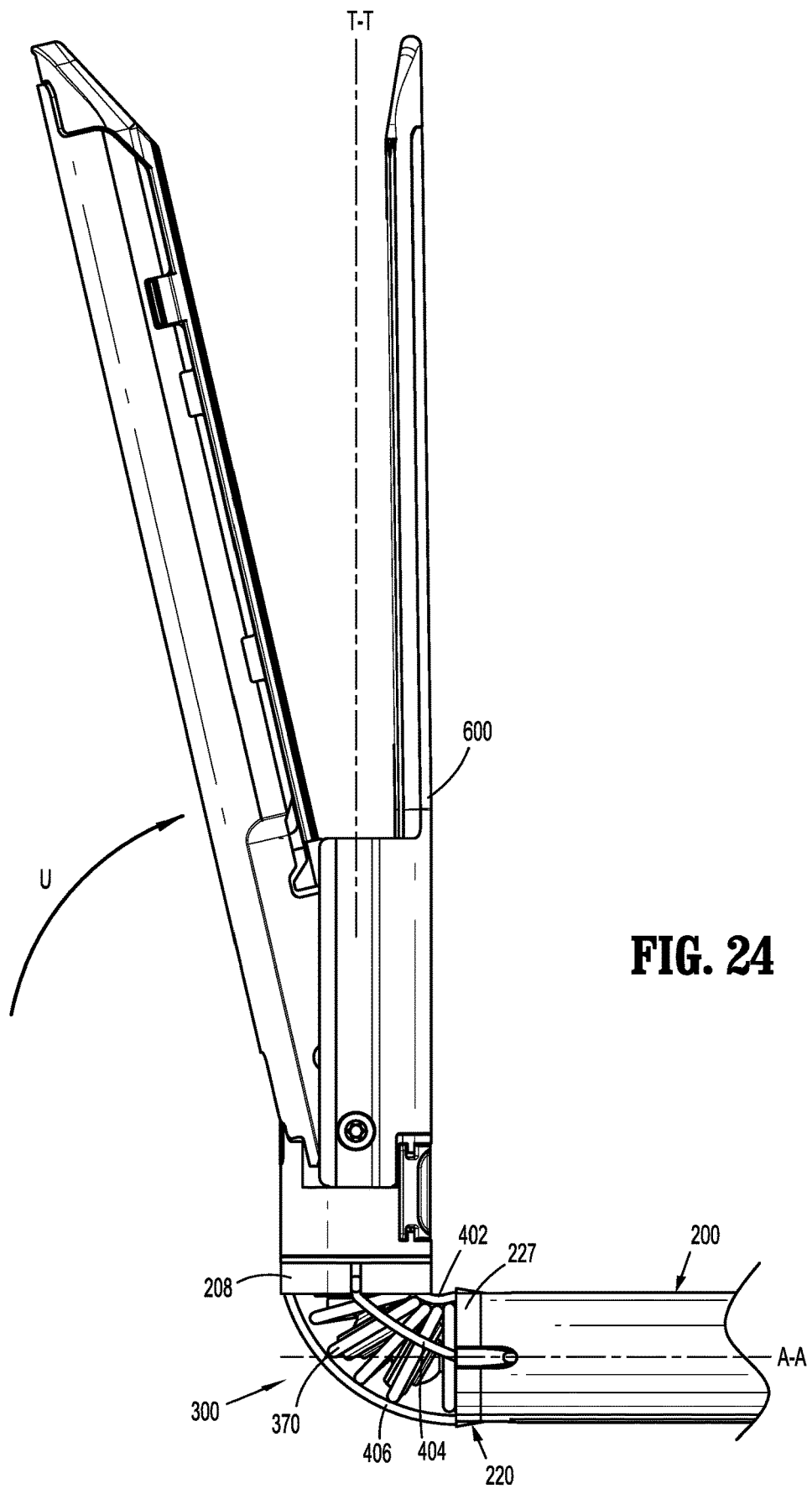
FIG. 24 is a side view of the tool assembly and the distal end of the adapter of FIG. 2 in an articulated position.
Figure 25:
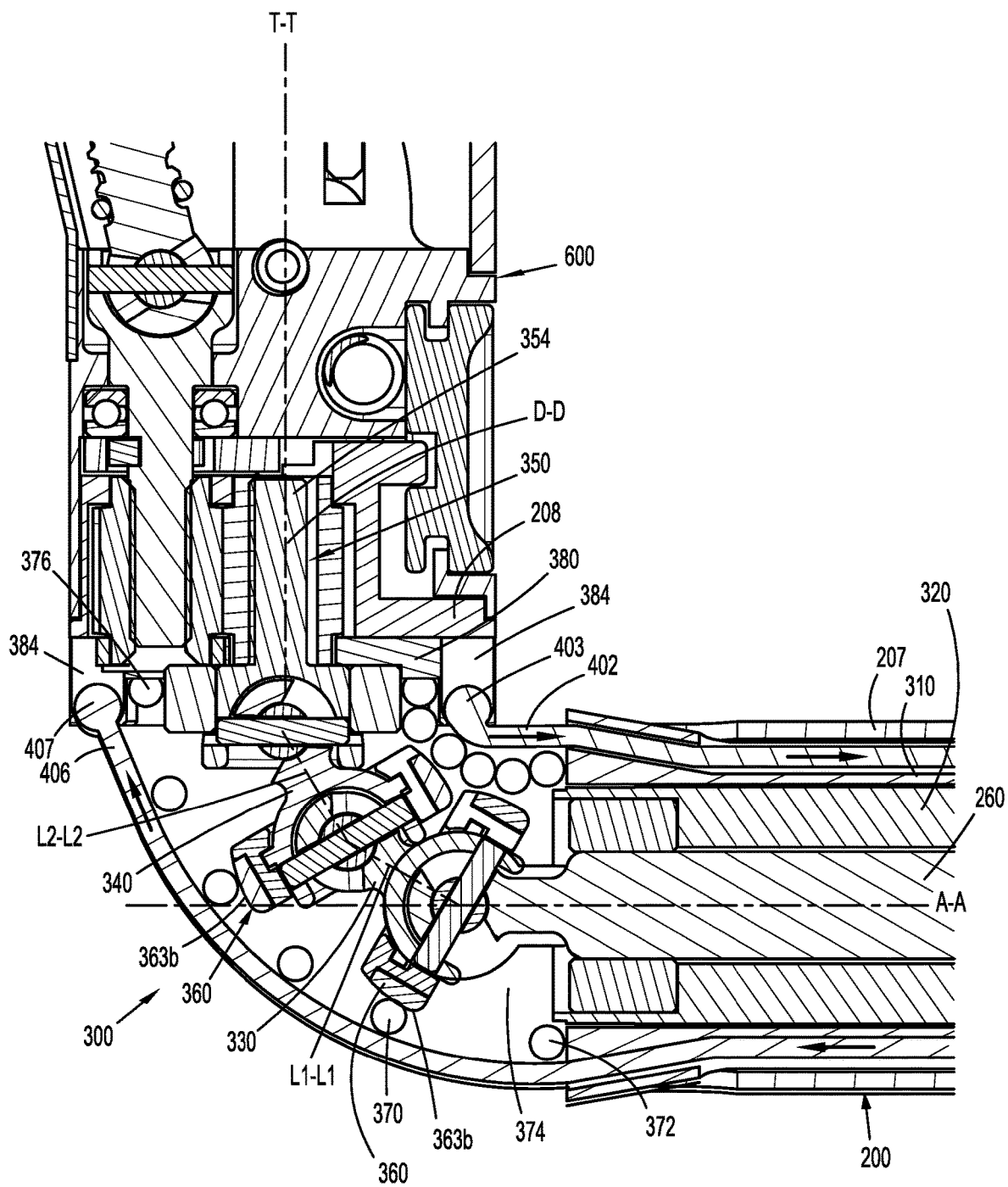
FIG. 25 is an enlarged longitudinal cross-sectional view of the joint assembly of FIG. 24 illustrating the joint assembly in an articulated position.

With reference to FIGS. 24 and 25, the adapter 200 (FIG. 2) includes the articulation mechanism 400 (FIG. 26) that manipulates the joint assembly 300. The articulation mechanism 400 and joint assembly 300 cooperate to control articulation of the joint assembly 300 before, during, and after actuation of the tool assembly 600. For example, when the tool assembly 600 is actuated to clamp tissue, fire staples through the clamped tissue, and/or sever tissue, the articulation mechanism 400 and joint assembly 300 cooperate to reduce chatter and maintain the position of the tool assembly 600 in relation to the adapter 200 during each function of the tool assembly 600.

To articulate the tool assembly 600 relative to the adapter 200, one or more of the articulation cables 402-408 is drawn proximally and one or more of the articulation cables 402-408 is released to extend distally and a diametrically positioned cable 402-408 is drawn proximally by the articulation mechanism 400. As shown, when the cable 402 is drawn proximally, the cable 406 is drawn distally such that the tool assembly 600 is articulated relative to the adapter 200 in the direction represented by arrow U to position the tool axis T-T at a 90° angle relative to the adapter axis A-A. Cables 404 and 408 (not shown) are unaffected by this movement; however, one of cables 404 or 408 may also be drawn proximally to draw the other one of cables 404 and 408 distally to articulate the tool assembly 600 relative to the adapter 200 in another plane such that the tool assembly 600 is articulable relative to the adapter 200 in a plurality of planes.

With particular reference to FIG. 25, as the cable 402 is drawn proximally, the ferrule 403 of the cable 402 draws the distal support 380 proximally to draw a portion of the distal support 380 towards the proximal support 320. As the cable 402 is drawn proximally, the cable 406 is released such that in response to the centering force of the spring cage 370, the portion of the distal support 380 opposite the cable 402 engages the ferrule 407 of cable 406 to draw the cable 406 distally. The articulation mechanism 400 is configured to draw cable 402 proximally and to draw cable 406 distally simultaneously such that the articulation of the distal support 380 relative to the proximal support 320 is controlled in a predictable manner.

As the distal support 380 articulates relative to the proximal support 320, the spring cage 370 controls the position of the link guides 360 to control uniform angles of articulation of each of the links 330, 340 and the distal drive shaft 350 relative to one another. Specifically, the spring cage 370 engages the outer surfaces 363b of the link guides 360, which are secured to the first and second links 330, 340, to control the angle of articulation of the first link 330 relative to the central drive shaft 260 represented by the angle of articulation of the first link axis L1-L1 relative to the adapter axis A-A, to be substantially equal to the angle of articulation of the second link 340 relative to the first link 330 represented by the angle of articulation of the second link axis L2-L2 relative to the first link axis L1-L1, and to be substantially equal to the angle of articulation of the distal drive shaft 350 relative to the second link 340 represented by the angle of articulation of the distal drive axis D-D relative to the second link axis L2-L2.

The centering force of the spring cage 370 and the engagement of the spring cage 370 with the outer surfaces 363b of the link guides 360 facilitates uniform articulation of each of the link guides 330, 340 such that each of the axes are angulated relative to one another at a substantially equal angle. For example as shown in FIG. 25, the first link 330 is articulated relative to the central drive shaft 260 such that the first link axis L1-L1 defines an angle of approximately 30° with the adapter axis A-A, the second link 340 is articulated relative to the first link 330 such that the second link axis L2-L2 defines an angle of approximately 30° with the first link axis L1-L1, and the distal drive shaft 350 is articulated relative to the second link 340 such that the distal drive axis D-D defines an angle of approximately 30° with the second link axis L2-L2. The sum of each of the angles defined between these axes is equal to the total articulation of the distal support 380 in relation to the adapter 200, and thus articulation of the tool assembly 600 which is secured to the distal support 380 in relation to the adapter 200. Thus, the distal drive axis D-D is articulated relative to the adapter axis A-A an articulation angle equal to a sum of the angles of articulation of the first link axis L1-L1 relative to the adapter axis A-A, the second link axis L2-L2 relative to the first link axis L1-L1, and the distal drive axis D-D relative to the second link axis L2-L2, e.g., 90° as shown.

To return the tool assembly 600 to the aligned position, the cable 402 is released such that the spring cage 370 moves the distal support 380 towards the aligned position. While the cable 402 is released, the cable 406 is drawn proximally in to provide stability to the joint assembly 300 as the distal support 380 returns to the aligned position.

Figure 26:
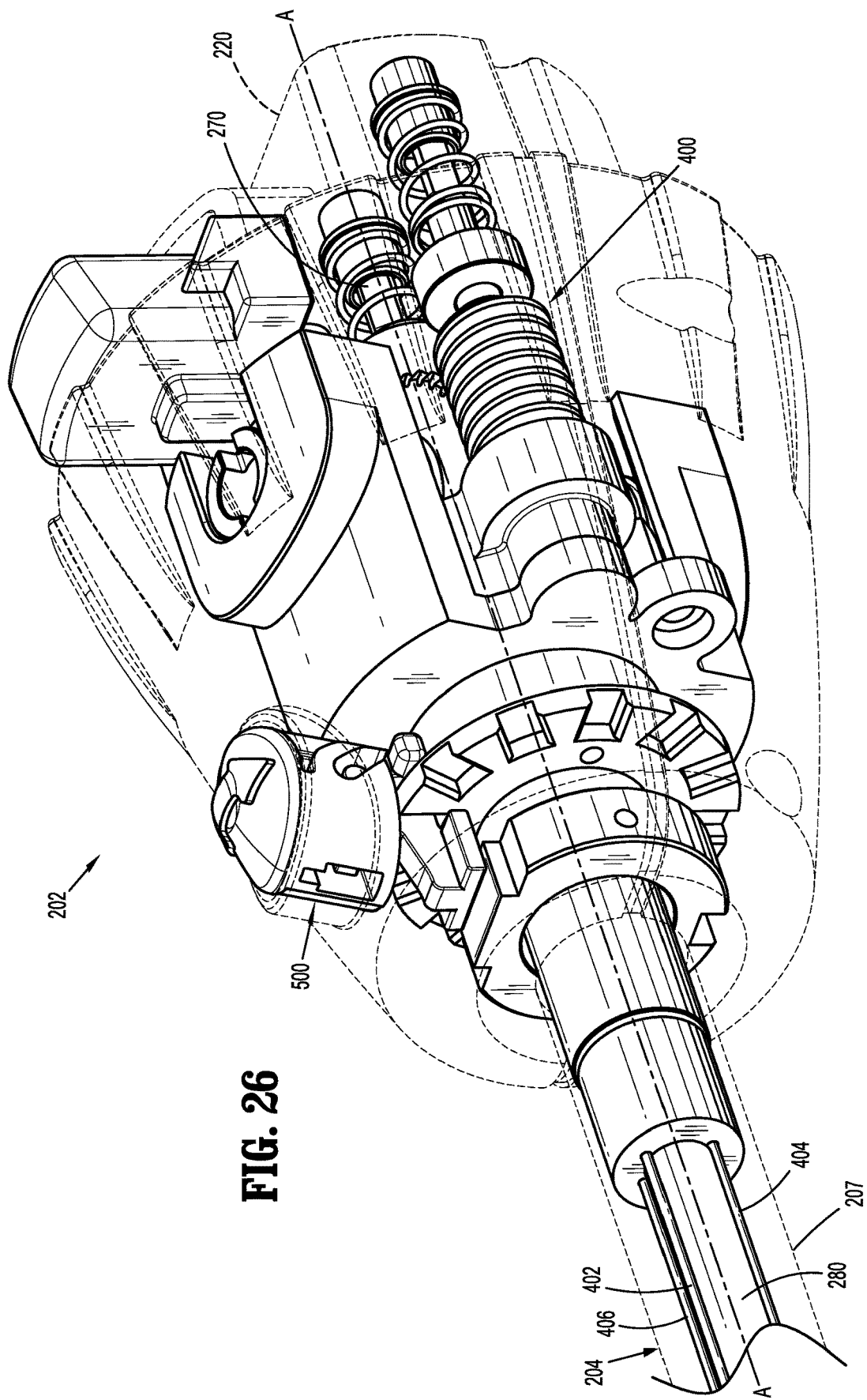
FIG. 26 is a perspective view of a proximal portion of the adapter of FIG. 2 with the outer tube and portions of the adapter shown in dashed lines to show a roll assembly and an articulation assembly.

Referring now to FIG. 26, the proximal portion 202 of the adapter 200 (FIG. 2) includes a connector 220, the articulation mechanism 400, and a roll mechanism 500. The connector 220 is secured to the proximal portion 202 of the adapter 200 and releasably couples the adapter 200 to the handle 100 (FIG. 1). The handle 100 is configured to facilitate rotation of the proximal drive shaft 270 and to manipulate the articulation mechanism 400 when the connector 220 is releasably coupled to the handle 100. The proximal drive shaft 270 extends along the adapter axis A-A of the adapter 200 and extends through the elongate portion 204 to effect rotation of the central drive shaft 260 (FIG. 12). The elongate portion 204 also includes a central tube 280 that is coaxially disposed about the proximal drive shaft 260 and the outer tube 207 coaxially disposed about the central tube 280 to define a channel 272 therebetween. The articulation mechanism 400 manipulates the articulation cables 402-408 to articulate the joint 300 (FIG. 3). For a detailed description of an exemplary proximal portion of an adapter having an articulation mechanism and a roll mechanism, reference may be made to commonly owned U.S. patent application Ser. No. 15/449,210, filed Mar. 3, 2017, the entire contents of which are hereby incorporated by reference.

Any of the components described herein may be fabricated from either metals, plastics, resins, composites or the like taking into consideration strength, durability, wearability, weight, resistance to corrosion, ease of manufacturing, cost of manufacturing, and the like.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A joint assembly comprising:
  a first support defining a first longitudinal axis;
  a second support defining a second longitudinal axis;
  a first drive shaft rotatably disposed along the first longitudinal axis and extending through the first support;
  a second drive shaft rotatably disposed along the second longitudinal axis and extending through the second support;
  a first link disposed between and coupled to each of the first and second drive shafts such that the first link rotates in response to rotation of the first drive shaft and the second drive shaft rotates in response to rotation of the first link;
  a second link disposed between and coupled to the first link and the second drive shaft, wherein rotation of the first link causes rotation of the second link to cause rotation of the second drive shaft;
  wherein the second support is adapted to be coupled to an articulation mechanism to facilitate articulation of the second support in relation to the first support; and
  a spring cage having a first end fixed to the first support and a second end fixed to the second support, the spring cage defining a spring channel between the first and second supports such that the first and second links and a portion of the first and second drive shafts are disposed within the spring channel, the spring cage operatively engaged with the first and second links to effect uniform articulation across the joint assembly in response to articulation of the second support relative to the first support.

2. The joint assembly according to claim 1, wherein the spring cage urges the first and second supports towards an aligned position in which the first and second longitudinal axes are coaxially aligned.

3. The joint assembly according to claim 1, wherein the spring cage engages the second link to effect uniform articulation across the joint assembly in response to articulation of the second support relative to the first support.

4. The joint assembly according to claim 1, wherein the first link defines a cavity that pivotally receives a portion of the first drive shaft and includes a distal ball.

5. The joint assembly according to claim 4, wherein the first link defines a first link axis that is coaxial with the first and second longitudinal axes in the aligned position, the spring cage controlling the first link in response to articulation of the second support relative to the first support such that the first link axis defines a first joint angle relative to the first longitudinal axis.

6. The joint assembly according to claim 4, wherein the second link defines a cavity that pivotally receives the distal ball of the first link, the second link including a distal ball pivotally received within the second drive shaft.

7. A joint assembly comprising:
a first support defining a first longitudinal axis;
a second support defining a second longitudinal axis;
a first drive shaft rotatably disposed along the first longitudinal axis and extending through the first support;
a second drive shaft rotatably disposed along the second longitudinal axis and extending through the second support;
a first link disposed between and coupled to each of the first and second drive shafts such that the first link rotates in response to rotation of the first drive shaft and the second drive shaft rotates in response to rotation of the first link, the first link defining a cavity that pivotally receives a portion of the first drive shaft and includes a distal ball;
a second link disposed between and coupled to the first link and the second drive shaft, wherein rotation of the first link causes rotation of the second link to cause rotation of the second drive shaft; and
a spring cage having a first end fixed to the first support and a second end fixed to the second support, the spring cage defining a spring channel between the first and second supports such that the first and second links and a portion of the first and second drive shafts are disposed within the spring channel, the spring cage operatively engaged with the first and second links to effect uniform articulation across the joint assembly in response to articulation of the second support relative to the first support;
wherein the first link defines a first link axis that is coaxial with the first and second longitudinal axes in the aligned position, the spring cage controlling the first link in response to articulation of the second support relative to the first support such that the first link axis defines a first joint angle relative to the first longitudinal axis; and a link guide disposed about the first link, the link guide directly engaged by the spring cage during articulation of the second support in relation to the first support to position the first link.

8. The joint assembly according to claim 7, wherein the link guide includes an inner collar and an outer collar, the inner collar forming a split ring defining a gap, the outer collar including an inner surface, the outer collar received over the ring of the inner collar such that the inner surface of the outer collar engages the ring of the inner collar to reduce the gap to secure the link guide to the first link.

9. The joint assembly according to claim 8, wherein the first link defines a disc positioned between the cavity and the distal ball and disposed orthogonally to the first link axis, the ring of the inner collar defining a groove that receives the disc to longitudinally secure the link guide relative to the first link.

10. The joint assembly according to claim 8, wherein the inner collar is formed of a resilient material and biased outwardly such that engagement between the ring of the inner collar and the inner surface of the outer collar fixes the inner and outer collars relative to one another.

11. The joint assembly according to claim 8, wherein the inner collar is formed of a plastic and the outer collar is formed of a metal.

12. The joint assembly according to claim 8, wherein the inner and outer collars are formed of a plastic.

13. The joint assembly according to claim 12, wherein the outer collar includes an outer surface having a friction reducing coating.

14. An adapter comprising:
a proximal portion configured to couple to a handle;
an elongate portion extending from the proximal portion and defining a first longitudinal axis; and
a distal portion supported by the elongate portion and configured to releasably couple a tool assembly to the handle, the distal portion including a joint assembly having:
a first support disposed along the first longitudinal axis;
a second support defining a second longitudinal axis;
a first drive shaft rotatably disposed along the first longitudinal axis and extending through the first support;
a second drive shaft rotatably disposed along the second longitudinal axis and extending through the second support;
a first link disposed between and coupled to each of the first and second drive shafts such that the first link rotates in response to rotation of the first drive shaft and the second drive shaft rotates in response to rotation of the first link;
a second link disposed between and coupled to the first link and the second drive shaft, wherein rotation of the first link causes rotation of the second link to cause rotation of the second drive shaft;
an articulation mechanism coupled to the second support and being operable to articulate the second support in relation to the first support; and
a spring cage having a first end fixed to the first support and a second end fixed to the second support, the spring cage defining a spring channel between the first and second supports such that the first and second links and a portion of the first and second drive shafts are disposed within the spring channel, the spring cage operatively engaged with the first and second links to effect uniform articulation across the joint assembly in response to articulation of the second support relative to the first support.

15. A surgical system, comprising:
a handle:
an adapter removably coupled to the handle, the adapter including:
  a proximal portion configured to couple to the handle;
  an elongate portion extending from the proximal portion and defining a first longitudinal axis; and
  a distal portion supported by the elongate portion, the distal portion including a joint assembly having:
    a first support disposed along the first longitudinal axis;
    a second support defining a second longitudinal axis;
    a first drive shaft rotatably disposed along the first longitudinal axis and extending through the first support;
    a second drive shaft rotatably disposed along the second longitudinal axis and extending through the second support;
    a first link disposed between and coupled to each of the first and second drive shafts such that the first link rotates in response to rotation of the first drive shaft and the second drive shaft rotates in response to rotation of the first link;
    a second link disposed between and coupled to the first link and the second drive shaft, wherein rotation of the first link causes rotation of the second link to cause rotation of the second drive shaft;
    an articulation mechanism coupled to the second support and being operable to articulate the second support in relation to the first support; and
    a spring cage having a first end fixed to the first support and a second end fixed to the second support, the spring cage defining a spring channel between the first and second supports such that the first and second links and a portion of the first and second drive shafts are disposed within the spring channel, the spring cage operatively engaged with the first and second links to effect uniform articulation across the joint assembly in response to articulation of the second support relative to the first support; and
a tool assembly removably coupled to the distal portion of the adapter.

* * * * *